US008202686B2

(12) United States Patent
Pamula et al.

(10) Patent No.: US 8,202,686 B2
(45) Date of Patent: *Jun. 19, 2012

(54) ENZYME ASSAYS FOR A DROPLET ACTUATOR

(75) Inventors: Vamsee K. Pamula, Durham, NC (US); Allen E. Eckhardt, Durham, NC (US); Jeremy Rouse, Raleigh, NC (US); Vijay Srinivasan, Durham, NC (US)

(73) Assignee: Advanced Liquid Logic, Inc., Research Triangle Park, NC (US)

( * ) Notice: Subject to any disclaimer, the term of this patent is extended or adjusted under 35 U.S.C. 154(b) by 254 days.

This patent is subject to a terminal disclaimer.

(21) Appl. No.: 12/497,677

(22) Filed: Jul. 5, 2009

(65) Prior Publication Data

US 2010/0041086 A1 Feb. 18, 2010

Related U.S. Application Data

(63) Continuation-in-part of application No. PCT/US2008/057959, filed on Mar. 23, 2008.

(60) Provisional application No. 60/896,341, filed on Mar. 22, 2007, provisional application No. 61/078,084, filed on Jul. 3, 2008, provisional application No. 61/149,808, filed on Feb. 4, 2009.

(51) Int. Cl.
*C12Q 1/00* (2006.01)
(52) U.S. Cl. .......................................................... 435/4
(58) Field of Classification Search ........................ 435/4
See application file for complete search history.

(56) References Cited

U.S. PATENT DOCUMENTS

| | | | |
|---|---|---|---|
| 5,559,134 A | 9/1996 | Buchmann et al. | |
| 5,753,186 A | 5/1998 | Hanley et al. | |
| 6,171,810 B1 | 1/2001 | Zhu | |
| 6,294,063 B1 | 9/2001 | Becker et al. | |
| 6,406,667 B1 * | 6/2002 | Singh et al. | 422/52 |
| 6,548,308 B2 * | 4/2003 | Ellson et al. | 436/180 |
| 6,565,727 B1 | 5/2003 | Shenderov | |
| 6,790,011 B1 | 9/2004 | Le Pesant et al. | |
| 7,052,244 B2 | 5/2006 | Fouillet et al. | |
| 7,109,222 B2 | 9/2006 | Cheng et al. | |
| 7,211,223 B2 | 5/2007 | Fouillet et al. | |
| 7,413,706 B2 | 8/2008 | Peeters et al. | |
| 7,458,661 B2 | 12/2008 | Kim et al. | |
| 7,531,072 B2 | 5/2009 | Roux et al. | |
| 7,569,129 B2 | 8/2009 | Pamula et al. | |
| 7,632,388 B2 | 12/2009 | Rikihisa et al. | |
| 7,875,160 B2 | 1/2011 | Jary | |
| 7,922,886 B2 | 4/2011 | Fouillet et al. | |
| 7,939,021 B2 * | 5/2011 | Smith et al. | 422/68.1 |
| 7,989,056 B2 | 8/2011 | Plissonnier et al. | |
| 8,075,754 B2 | 12/2011 | Sauter-Starace et al. | |
| 2002/0102737 A1 | 8/2002 | Millington et al. | |
| 2003/0148538 A1 * | 8/2003 | Ng | 436/180 |
| 2003/0170698 A1 | 9/2003 | Gascoyne et al. | |
| 2004/0055891 A1 | 3/2004 | Pamula et al. | |
| 2004/0209253 A1 | 10/2004 | Tam | |
| 2005/0031657 A1 | 2/2005 | Gilson et al. | |
| 2005/0106742 A1 | 5/2005 | Wahl | |
| 2005/0158845 A1 | 7/2005 | Wikswo et al. | |
| 2006/0054503 A1 | 3/2006 | Pamula et al. | |
| 2006/0078893 A1 | 4/2006 | Griffiths et al. | |
| 2006/0254933 A1 | 11/2006 | Adachi et al. | |
| 2010/0151439 A1 * | 6/2010 | Pamula et al. | 435/4 |

FOREIGN PATENT DOCUMENTS

| | | |
|---|---|---|
| JP | 5025159 A | 2/1993 |
| WO | 0207503 | 1/2002 |
| WO | WO0218539 A2 | 3/2002 |
| WO | 2004030820 | 4/2004 |
| WO | 2006081558 A2 | 8/2006 |
| WO | 2006127451 A3 | 11/2006 |
| WO | 2006138543 | 12/2006 |
| WO | 2007123908 A2 | 1/2007 |
| WO | 2007048111 | 4/2007 |
| WO | 2007120240 A2 | 10/2007 |
| WO | 2007120241 A2 | 10/2007 |
| WO | WO 2007/120241 A3 * | 10/2007 |
| WO | 2008051310 A2 | 5/2008 |
| WO | 2008055256 | 5/2008 |
| WO | 2008091848 A2 | 7/2008 |
| WO | 2008098236 A2 | 8/2008 |
| WO | 2008106678 A1 | 9/2008 |
| WO | 2008112856 A1 | 9/2008 |

OTHER PUBLICATIONS

Huebner A. et al. Static Microdroplet Arrays. Lab on a Chip 9, 692-698, 2009.*
Henry C. Trapping Cells and Organelles. C&EN 83(10)7 Mar. 7, 2005.*

(Continued)

*Primary Examiner* — Ralph Gitomer
(74) *Attorney, Agent, or Firm* — William A. Barrett; Ward & Smith, PA

(57) ABSTRACT

The invention relates to a microfluidic platform and methods of using the platform for conducting enzyme assays using a droplet actuator. The enzyme assays of the invention are useful for, among other things, identifying and/or characterizing disorders resulting from conditions in which enzymes are defective or are produced in inappropriate amounts. Enzyme assays of the invention may, for example, be used to detect altered activity of a particular enzyme in a sample, which may serve as an indicator of a particular disease. Altered activity may, for example, be caused by conditions which result in the increased or reduced production of a certain enzyme or its substrate and/or conditions which result in defective enzymes and/or substrates exhibiting increased or decreased effectiveness relative to corresponding normal enzymes and/or substrates.

115 Claims, 15 Drawing Sheets

OTHER PUBLICATIONS

Jie Ding, "System level architectural optimization of semi-reconfigurable microfluidic system," M.S. Thesis, Duke University Dept of Electrical Engineering, 2000.

Moon, Hyejin, Ph.D., "Electrowetting-on-dielectric microfluidics: Modeling, physics, and MALDI application," University of California, Los Angeles, 2005.

Vijay Srinivasan, Vamsee K. Pamula, Richard B. Fair, "An integrated digital microfluidic lab-on-a-chip for clinical diagnostics on human physiological fluids," Lab on a Chip (LOC), vol. 4, pp. 310-315, 2004.

Wiederschain G., Raghavan S., Kolodny E., "Characterization of 6-hexadecanoylamino-4-methylumbelliferyl-β-D-galactopyranoside as fluorogenic substrate of galactocerebrosidase for the diagnosis of Krabbe disease", (1992) Clinica Chimica Acta, 205 (1-2), pp. 87-96.

Svennerholm, Lars et al., Clinica Chimica Acta, vol. 106, Issue 2, Sep. 25, 1980, pp. 183-193; "Assay of the β-glucosidase activity with natural labelled and artificial substrates in leukocytes from homozygotes and heterozygotes with the norrbottnian type (type 3) of Gaucher disease".

Broadhead et al., Clinica Chemica Acta, vol. 75, Issue 1, Feb. 15, 1977, pp. 155-161, "The diagnosis of gaucher's disease in liver using 4-methylumbellifery1-β-d-glucopyranoside".

Besley G.T.N., Moss S.E., "Studies on sphingomyelinase and β-glucosidase activities in Niemann-Pick disease variants. Phosphodiesterase activities measured with natural and artificial substrates", (1983) Biochimica et Biophysica Acta—Lipids and Lipid Metabolism, 752 (1), pp. 54-64.

Murphey, William H. et al., "Screening tests for argininosuccinic aciduria, orotic aciduria, and other inherited enzyme deficiencies using dried blood specimens", Biochemical Genetics, vol. 6, No. 1, pp. 51I-59, DOI: 10.1007/BF00485965, 1972, pp. 51-59.

Hopwood, et a., "A fluorometric assay using 4-methylumbelliferyl alpha-L-iduronide for the estimation of alpha-L-iduronidase activity and the detection of Hurler and Scheie syndromes," Clin Chim Acta. 92(2): pp. 257-265, 1979.

Fair et al., "Integrated Chemical/Biochemical Sample Collection, Pre-Concentration, and Analysis on a Digital Microfluidic Lab-on-a-Chip Platform," Lab-on-a-Chip: Platforms, Devices, and Applications, Conf. 5591, SPIE Optics East, Philadelphia, Oct. 25-28, 2004.

Hoshiyama et al., "Complexation and proton dissociation behavior of 7-hydroxy-4-methylcoumarin and related compounds in the presence of β-cyclodextrin", Journal of Photochemistry and Photobiology A: Chemistry 138 (2001), pp. 227-233.

Srinivasan et al., "Protein Stamping for MALDI Mass Spectrometry Using an Electrowetting-Based Microfluidic Platform," Lab-on-a-Chip: Platforms, Devices, and Applications, Conf. 5591, SPIE Optics East, Philadelphia, Oct. 25-28, 2004.

Broadhead et al., "The diagnosis of gaucher's disease in liver using 4-methylumbelliferyl-β-d-glucopyranoside," Clinica Chemica Acta, vol. 75, Issue 1, Feb. 15, 1977, pp. 155-161.

Besley et al., "Studies on sphingomyelinase and β-glucosidase activities in Niemann-Pick disease variants. Phosphodiesterase activities measured with natural and artificial substrates", (1983) Biochimica et Biophysica Acta—Lipids and Lipid Metabolism, 752 (1), pp. 54-64.

Boggs, Dallas E., "Detection of Inborn Errors of Metabolism", Critical Reviews in Clinical Laboratory Sciences 1971, vol. 2, No. 4 : pp. 529-572.

Ding, Jie, "System level architectural optimization of semi-reconfigurable microfluidic system," M.S. Thesis, Duke University Dept of Electrical Engineering, 2000.

Fouillet et al., "Digital microfluidic design and optimization of classic and new fluidic functions for lab on a chip systems," Microfluid Nanofluid, vol. 4, pp. 159-165 (2008).

Henry, C., "Trapping Cells and Organelles", C&EN 83(10)7, Mar. 7, 2005.

Hopwood et al., "A fluorometric assay using 4-methylumbelliferyl alpha-L-iduronide for the estimation of alpha-L-iduronidase activity and the detection of Hurler and Scheie syndromes," Clin Chim Acta. 92(2): pp. 257-265, 1979.

Huebner A., et al., "Static Microdroplet Arrays", Lab-on-a-Chip, pp. 692-698, 2009.

Moon, Hyejin, Ph.D., "Electrowetting-on-dielectric microfluidics: Modeling, physics, and MALDI application," Ph.D. Dissertation, University of California, Dept. of Mechanical Engineering, Los Angeles, 2006.

Murphey et al., "Screening tests for argininosuccinic aciduria, orotic aciduria, and other inherited enzyme deficiencies using dried blood specimens", Biochemical Genetics, vol. 6, No. 1, pp. 51I-59, DOI: 10.1007/BF00485965 (1972).

Pollack et al., "Electrowetting-Based Actuation of Droplets for Integrated Microfluidics," Lab on a Chip (LOC), vol. 2, pp. 96-101, 2002.

Srinivasan et al., "An integrated digital microfluidic lab-on-a-chip for clinical diagnostics on human physiological fluids," Lab on a Chip (LOC), vol. 4, pp. 310-315, 2004.

Svennerholm et al., "Assay of the β-glucosidase activity with natural labelled and artificial substrates in leukocytes from homozygotes and heterozygotes with the norrbottnian type (type 3) of Gaucher disease," Clinica Chimica Acta, vol. 106, Issue 2, Sep. 25, 1980, pp. 183-193.

Voznyi et al., A fluorimetric enzyme assay for the diagnosis of MPS II (Hunter disease)), J. Inhert. Metab. Dis., Vo. 24(6), pp. 675-680, 2001.

Wiederschain et al., "Characterization of 6-hexadecanoylamino-4-methylumbelliferyl-β-D-galactopyranoside as fluorogenic substrate of galactocerebrosidase for the diagnosis of Krabbe disease", (1992) Clinica Chimica Acta, 205 (1-2), pp. 87-96.

Terry et al., "A Gas Chromatographic Air Analyzer Fabricated on a Silicon Wafer," IEEE Transactions on Electron Devices, vol. ED-26, 1979, pp. 1880-1886.

Tuckerman et al., "High-Performance Heat Sinking for VLSI," IEEE Electron Device Letters, 1981, pp. 126-129.

Batchelder, J.S., "Dielectrophoretic manipulator," Review of Scientific Instruments, vol. 54, 1983, pp. 300-302.

Manz et al., "Miniaturized Total Chemical Analysis Systems: a Novel Concept for Chemical Sensing," Sensors and Actuators B: Chemical, 1990, pp. 244-248.

Welters et al., "Fast Electrically Switchable Capillary Effects," Langmuir, vol. 14, Mar. 1998, pp. 1535-1538.

McDonald et al., "Fabrication of Microfluidic systems in poly (dimethylsiloxane)," Electrophoresis, vol. 21, 2000, pp. 27-40.

Wego et al., "Fluidic microsystems based on printed circuit board technology," Journal of Micromechanics and Microengineering, vol. 11, No. 5, pp. 528-531 (Sep. 2001).

Moon et al., "Low voltage electrowetting-on-dielectric," Journal of Applied Physics, vol. 92 (7): pp. 4080-4087, Oct. 1, 2002.

Locascio et al. "Polymer microfluidic devices," Talanta, vol. 56, Feb. 2002, pp. 267-287.

Yoon et al., "Preventing Biomolecular Adsorption in Electrowetting-Based Biofluidic Chips," Analytical Chemistry, vol. 75, Oct. 2003, pp. 5097-5102.

Chiou et al., "Light actuation of liquid by optoelectrowetting," Sensors and Actuators A: Physical, vol. 104, May 2003, pp. 222-228.

Squires et al., "Microfluidics: Fluid physics at the nanoliter scale," Reviews of Modern Physics, vol. 77, Oct. 2005, pp. 977-1-26.

Fouillet et al., "Design and Validation of a Complex Generic Fluidic Microprocessor Based on EWOD Droplet for Biological Applications," 9th International Conference on Miniaturized Systems for Chemistry and Life Sciences (MicroTAS), Boston, MA: 2005, pp. 58-60.

Guttenberg et al., "Planar chip devices for PCR and hybridization with surface acoustic wave pump.," Lab on a chip, vol. 5, Mar. 2005, pp. 12617-12622.

Yager et al., "Microfluidic diagnostic technologies for global public health," Nature, vol. 442, 2006, pp. 412-418.

Cooney et al.,"Electrowetting droplet microfluidics on a single planar surface," Microfluidics and Nanofluidics, vol. 2 Mar. 2006, pp. 435-446.

Chatterjee et al., "Droplet-based microfluidics with nonaqueous solvents and solutions.," Lab on a Chip, vol. 6, Feb. 2006, pp. 199-206.

Madou et al. "Lab on a CD," Annual Review of Biomedical Engineering, vol. 8, pp. 601-628, 2006.

Yi et al., "Characterization of electrowetting actuation on addressable single-side coplanar electrodes," Journal of Micromechanics and Microengineering, vol. 16, Oct. 2006, pp. 2053-2059.
Dubois et al., "Ionic Liquid Droplet as e-Microreactor," Analytical Chemistry, vol. 78, 2006, pp. 4909-4917.
Whitesides, G.M., "The origins and the future of microfluidics," Nature, vol. 442, 2006, pp. 368-373.
Chin et al., "Lab-on-a-chip devices for global health: past studies and future opportunities.," Lab on a Chip, vol. 7, Jan. 2007, pp. 41-57.
Baviere et al., "Dynamics of droplet transport induced by electrowetting actuation," Microfluidics and Nanofluidics, vol. 4, May 2007, pp. 287-294.
Paik et al., "A Digital-Microfluidic Approach to Chip Cooling," IEEE Design & Test of Computers, vol. 25, Jul. 2008, pp. 372-381.
Tey et al., "Droplet microfluidics.," Lab on a chip, vol. 8 Feb. 2008, pp. 198-220.
Barbulovic-Nad et al., "Digital microfluidics for cell-based assays.," Lab on a chip, vol. 8, Apr. 2008, pp. 519-526.
Huebner et al., "Microdroplets: a sea of applications?," Lab on a Chip, vol. 8, Aug. 2008, pp. 1244-1254.
Gong et al., "Direct-referencing two-dimensional-array digital microfluidics using multi-layer printed circuit board," Journal of Microelectromechanical Systems, vol. 17, Jan. 2008, pp. 257-264.
Miller et al., "A Digital Microfluidic Approach to Homogeneous Enzyme Assays," Analytical Chemistry, vol. 80, 2008, pp. 1614-1619.
Sista et al., "Heterogeneous immunoassays using magnetic beads on a digital microfluidic platform," Lab on a Chip, vol. 8, Dec. 2008, pp. 2188-2196.
Sista et al., "Development of a digital microfluidic platform for point of care testing.," Lab on a chip, vol. 8, Dec. 2008, pp. 2091-2104.
Luk et al., "Pluronic additives: a solution to sticky problems in digital microfluidics," Langmuir: the ACS journal of surfaces ans colloids, vol. 24, Jun. 2008, pp. 6382-6389.
Luan et al., "Integrated Optical Sensor in a Digital Microfluidic Platform," IEEE Sensors Journal, vol. 8, May 2008, pp. 628-635.
Mariella, R. "Sample preparation: the weak link in microfluidics-based biodetection.," Biomedical Microdevices, vol. 10, Dec. 2008, pp. 777-784.
Brassard et al., "Water-oil core-shell droplets for electrowetting-based digital microfluidic devices.," Lab on a chip, vol. 8, Aug. 2008, pp. 1342-1349.
Mukhopadhyay, R. "Microfluidics: on the slope of enlightenment.," Analytical chemsitry vol. 81, Jun. 2009, pp. 4169-4173.
Mousa et al., "Droplet-scale estrogen assays in breast tissue, blood, and serum.," Science Translational Medicine, vol. 1 Oct. 2009, p. Ira2.
Poulos et al., "Electrowetting on dielectric-based microfluidics for integrated lipid bilayer formation and measurement," Applied Physics Letters, vol. 95, 2009, p. 013706.
Langelier et al., "Acoustically driven programmable liquid motion using resonance cavities" Proceedings of the National Academy of Sciences of the USA, vol. 106, Aug. 2009, pp. 12617-12622.

Malic et al., "Biochip functionalization using electrowetting-on-dielectric digital microfluidics for surface plasmon resonance imaging detection of DNA hybridization.," Biosensors & Bioelectronics, vol. 24, Mar. 2009, pp. 2218-2224.
Shah et al., "EWOD-driven droplet microfluidic device integrated with optoelectronic tweezers as an automated platform for cellular isolation and analysis.," Lab on a Chip, vol. 9, Jun. 2009, pp. 1732-1739.
Yang et al.,"Manipulation of droplets in microfluidic systems," Trends in Analytical Chemistry, vol. 29, Feb. 2010, pp. 141-157.
Haeberle et al., "Microfluidic lab-on-a chip platforms: requirements, characteristics and applications," Chemical Society reviews, vol. 39, Mar. 2010, pp. 1153-1182.
Coltro et al., "Toner and paper-based fabrication techniques for microfluidic applications," Electrophoresis, vol. 31, Jul. 2010, pp. 2487-2498.
Jebrail et al., "Lets get digital: digitizing chemical biology with microfluidics.," Current Opinion in Chemical Biology, vol. 14, Oct. 2010, pp. 574-581.
Malic et al., "Integration and detection of biochemical assays in digital microfluidic LOC devices," Lab on a chip, vol. 10, Feb. 2010, pp. 418-431.
Hua et al., "Multiplexed real-time polymerase chain reaction on a digital microfluidic platform.," Analytical Chemistry, vol. 82, Mar. 2010, pp. 2310-2316.
Shin et al., "Machine vision for digital microfluidics," Review of Scientific Instruments, vol. 81, 2010, p. 014302.
Millington et al., "Digital microfluidics: a future technology in the newborn screening laboratory?," Seminars in Perinatology, vol. 34, Apr. 2010, pp. 163-169.
Wulf-Burchfield et al., "Microfluidic platform versus conventional real-time polymerase chain reaction for the detection of Mycoplasma pneumonia in respiratory specimans.," Diagnostic Micobiology and Infectious disease, vol. 67, May 2010, pp. 22-29.
Barbulovic-Nad et al., "A microfluidic platform for complete mammalian cell culture," Lab on a chip, vol. 10, Apr. 2010, pp. 1536-1542.
Becker, H., "Mind the gap!," Lab on a chip, vol. 10, Feb. 2010, pp. 271-273.
Kim et al., "Electrowetting on paper for electronic paper display," ACS Applied Materials & Interfaces, vol. 2 Nov. 2010, pp. 3318-3323.
Park et al., "Single-sided continuous optoelectrowetting (SCOEW) for droplet manipulation with light patterns.," Lab on a chip, vol. 10, Jul. 2010, pp. 1655-1661.
Welch, et al., "Picoliter DNA sequencing chemistry on an electrowetting-based digital microfluidic platform.," Biotechnology journal, vol. 6, Feb. 2011, pp. 165-176.
Vaitkus et al., "Inhibition of cyclodextrin acid hydrolysis by some inclusion complexes," J. Incl Phenom Macrocycl Chem, 2010.
Wagner, "The Effects of Cyclodextrins on Guest Fluorescence," Ch. 2, Cyclodextrin Materials Photochemistry, Photophysics and Photobiology, 2006.

\* cited by examiner

US 8,202,686 B2

ENZYME ASSAYS FOR A DROPLET ACTUATOR

RELATED PATENT APPLICATIONS

This application is a continuation-in-part of International Patent Application No. PCT/US2008/57959, entitled "Enzymatic Assays for a Droplet Actuator," filed on Mar. 23, 2008, pending, which claims priority to, is related to, and incorporates by reference U.S. Patent Application No. 60/896,341, entitled "Enzymatic Assays for a Droplet Microactuator," filed on Mar. 22, 2007. This application also claims priority to, is related to, and incorporates by reference U.S. Patent Application No. 61/078,084, entitled "Platform for Detection of Deficiencies in Enzymatic Activity," filed on Jul. 3, 2008 and U.S. Patent Application No. 61/149,808, entitled "Droplet-Based Platform for Evaluating Enzymatic Activity," filed on Feb. 4, 2009.

GOVERNMENT INTEREST

This invention was made with government support under HD057713, DK066956, and GM072155 awarded by the National Institutes of Health of the United States. The United States Government has certain rights in the invention.

BACKGROUND

Newborn infants are routinely tested for various genetic disorders. These tests are expensive, and typically only a small fraction of possible disorders are included in the testing regimen. At least 50 lysosomal storage disorders are rarely tested. Some of these disorders are extremely rare. Pathologies often involve significant physical and mental debilitation leading to death. Therapies are available in some cases. Outcomes may be improved with early diagnosis and treatment. Pompe disease, for example, results from a deficiency in alpha-glucosidase. Enzyme replacement therapy is available for treating the condition. However, newborns are rarely screened for Pompe.

Testing of newborn infants typically involves collecting a sample of blood from the heel of a baby. The sample is placed on a card, dried to yield a dried blood sample (DBS). The DBS is transported to a central laboratory for testing, where it is used as input for assays for several metabolic and other disorders. Using the current DBS testing methodologies, a prohibitively large volume of blood would be required in order to do a significantly larger number of tests.

There is a need for testing methods that are highly sensitive and require only a small volume of blood.

Droplet actuators are used to effect droplet operations. A droplet actuator typically includes one or more substrates configured to form a droplet operations surface or gap for conducting the droplet operations. The one or more substrates may be associated with electrodes for mediating the droplet operations. The droplet operations surface or gap is typically filled or coated with a filler fluid that is immiscible with the liquid that is to be subjected to droplet operations. There is a need in the art for techniques for conducting enzyme assays which make use of the advantages of droplet actuators.

BRIEF DESCRIPTION OF THE INVENTION

The invention provides a method of conducting a droplet-based enzyme assay. The method may include providing liquid droplets including a sample droplet including an enzyme of interest and one or more reagent droplets including a substrate which is potentially modified in the presence of the enzyme yielding one or more signal-producing products. The droplets may be submerged in a liquid which is immiscible with the droplets. The one or more reagent droplets may include any reagents useful to produce the desired activity of the target enzyme. The method may include combining the sample droplet and the one or more reagent droplets in the immiscible liquid to yield a reaction droplet effecting an enzyme reaction in the immiscible liquid. The method may include measuring any signal produced by the one or more signal producing products. Steps in the method may be accomplished without removing the sample droplet, one or more reagent droplets, or reaction droplet from the immiscible liquid. One or more electrodes may be used to mediate dispensing of the sample droplet and/or dispensing of the one or more reagent droplets. One or more electrodes for combining the sample droplets and the one or more reagent droplets. The one or more electrodes may be provided as components of a droplet actuator. Droplet operations may, in some cases, be mediated on a droplet operations surface and/or in a droplet operations gap of a droplet actuator.

The reaction droplet may be divided into two or more sub-droplets. One or more electrodes may be used to mediate the dividing of the reaction droplet. One or more of the sub-droplets may be immediately combined with a quenching droplet to yield one or more droplets to assess product generation at the onset of reaction (time 0 droplets). Signal may be detected from the one or more time 0 droplets. One or more of the sub-droplets may be incubated for a predetermined period of time. One or more incubating droplets may be combined with one or more quenching droplets to yield one or more endpoint droplets. Signal may be detected from the one or more endpoint droplets. The method may include assessing modification of the substrate by the enzyme of interest based on differences in signal in the time 0 droplet and the endpoint droplet.

In some embodiments, the method includes providing multiple sample droplets including an enzyme of interest. The method may include incubating two or more of the sample droplets for different periods of time. The method may include measuring rates of reaction or endpoint signals for each of the two or more of the sample droplets. The method may include constructing a curve using the rates of reaction or endpoint signals. The method may include calculating enzyme activity based on the curve.

In some embodiments, the sample droplet used in an enzyme assay of the invention has a volume which is less than about 5000 nL; or less than about 1000 nL; or less than about 500 nL; or less than about 250 nL; or less than about 100 nL. In some embodiments, the one or more reagent droplets used in an enzyme assay of the invention each has a volume which is less than about 1000 nL; or less than about 500 nL; or less than about 250 nL; or less than about 100 nL. In some embodiments, the reaction droplet, which results from a combination of one or more of the sample droplet and one or more of the reagent droplets, has a volume which is less than about 2500 nL; or less than about 1000 nL; or less than about 750 nL; or less than about 500 nL.

In various assays of the invention, the enzyme of interest being targeted is suspected of exhibiting altered enzyme activity as compared to a corresponding normal enzyme or of being present in an amount which differs from the normal range. The method is useful for providing diagnostic information. For example, the method may include conducting an assay according to any of the methods of the invention, wherein sample droplet includes a clinical sample from a subject including the enzyme of interest; and providing diagnostic information based on the activity of the enzyme of interest from the human clinical sample. The diagnostic information may include information diagnostically relevant to a glycogen storage disease or a lysosomal storage disease. In some cases, the deficiency is in the activity of a glycosidase, such as α-glucosidase or α-galactosidase activity. In some embodiments, the assay is conducted and the diagnostic information is provided at a point of sample collection. The point of sample collection may, for example, be in the presence of, or in proximity to, a subject.

Various biological samples may be used. Examples include blood, plasma, serum, tears, saliva, and urine. Many other examples are described herein. In some cases, the clinical sample includes a dried blood sample. In some cases, the clinical sample includes a fresh blood sample.

A fresh blood sample may be collected from the subject and immediately loaded onto a droplet actuator for conducting the assay. In some embodiments, time from collection of the blood sample to providing diagnostic information is less than about 12 hours; or 6 hours. Samples may include human clinical sample or non-human animal samples.

In certain embodiments, the substrate includes a glycoside substrate. In some cases, the substrate releases a fluorophore upon contact with the enzyme of interest. In some embodiments, two or more assays are conducted simultaneously using different fluorophores for each enzyme tested. In some cases, the fluorophore includes 4-methylumbelliferyl.

The substrate may, for example, include a glycoside substrate which releases a fluorophore upon contact with the enzyme of interest. The substrate may, for example, include a glycoside substrate including glucose, galactose, fucose, mannose, sialic acid, hexose, hexosamine and/or N-acetylated hexosamine. In some embodiments, the substrate includes a 4-methylumbelliferyl glycoside. Examples include 4-methylumbelliferyl-α-L-iduronide, 4-methylumbelliferyl-β-D-galactoside, 4-methylumbelliferyl-β-D-glucuronic acid, 4-methylumbelliferyl-α-L-fucoside, 4-methylumbelliferyl-α-mannoside, 4-methylumbelliferyl-β-D-mannoside, 4-nitrocathecol sulfate, 4-methylumbelliferyl-β-D-N-acetylglucosaminide, 4-methylumbelliferyl-β-D-N-acetylglucosaminide sulfate, 4-methylumbelliferyl-β-D-glucosaminide, 4-methylumbelliferyl-β-D-galactoside, 4-methylumbelliferyl-α-D-neuraminic acid, 4-methylumbelliferyl-α-D-N-acetylgalactosaminide, phenolphthalein β-D-glucuronic acid. Other substrates and detection modalities are described herein.

In some embodiments, the invention includes reducing or eliminating reaction contaminants associated with the substrate prior to yielding the assay droplet. This may, for example, be achieved by photobleaching the substrate prior to yielding the assay droplet. In some cases, the photobleaching is effected prior to providing the droplet including the substrate on the droplet actuator. In other cases, the photobleaching is effected after to providing the droplet including the substrate on the droplet actuator. In one embodiment, the reducing or eliminating reaction contaminants is conducted using a 4-methylumbelliferyl glycoside substrate.

In various embodiments, the droplets used in the enzyme assay are in contact with or submerged in a liquid which is immiscible with the droplets. The droplets may also, in some cases, be sandwiched in a droplet operations gap. The immiscible liquid may, for example, include an oil, such as a silicone oil or paraffin that is liquid at the reaction temperature. The filler fluid may include a surfactant. The surfactant may, for example, be a nonionic low hydrophile-lipophile balanced (HLB) surfactant. In some cases, the HLB of the surfactant is less than about 10 or less than about 5. Examples of suitable surfactants include Triton X-15; Span 85; Span 65; Span 83; Span 80; Span 60; and fluorinated surfactants.

In some embodiments, the sample droplet includes a reconstituted blood sample. In multiplexing applications, the blood sample may be reconstituted using a single universal reconstitution solution, and the blood sample is divided to yield two or more reaction droplets. Two or more of the reaction droplets may each be combined with one or more sets of one or more reagent droplets, each such set including reagents selected for establishing reaction conditions for a different enzyme assay. The universal reconstitution solution may, for example, be a saline solution or water, or any other solution which includes components that do not sufficiently interfere with any of the intended enzyme reactions to render such reactions unsuited for their intended purpose, e.g., diagnosis or screening for an enzyme disorder. Each of two or more sample droplets with reagent droplets are selected for establishing reaction conditions for a different enzyme assay. In some embodiments, the sample droplets include fresh blood and/or reconstituted blood spot; a dried blood spot reconstituted in water; a dried blood spot reconstituted in a saline solution; a dried blood spot reconstituted in a buffer; and/or dried blood spot reconstituted in a solution including a surfactant. The surfactant may, for example, have an HLB in the range of about 10 to about 20 or about 15 to about 20. In some cases the multiplexed sample droplets are from the same subject; in other cases, the sample droplets are from different subjects. In some cases the multiplexed enzyme reactions include reactions with conditions suitable for screening or testing for Pompe, Niemann-Pick, Fabry, Krabbe, Maroteaxu-Lamy, Hunter, Hurler, and Gaucher.

Where a dried blood spot is used, the sample droplet is prepared by reconstituting a dried blood spot disc. In some cases, the disc has a diameter of less than about 10 mm and is reconstituted in less than about 1000 μL of solution; or less than about 750 μL of solution; or less than about 500 μL of solution; or less than about 250 μL of solution; or ranging from about 25 μL to about 750 μL; or ranging from about 25 μL to about 500 μL; or ranging from about 25 μL to about 250 μL; or ranging from about 25 μL to about 150 μL. In some cases, the sample is dispensed into at least 5 sample droplets; or at least 10 sample droplets; or at least 25 sample droplets; or at least 40 sample droplets. In some cases, the dried blood spot disc has a diameter ranging from about 1 mm to about 15 mm; or from about 1 mm to about 8 mm; or from about 1 mm to about 6 mm; or from about 1 mm to about 4 mm. The disc is prepared by depositing blood on a substrate. In one embodiment, the dried blood spot is made using less than about 10 mL of blood or less than about 1 mL of blood or less than about 100 μL. In some cases, the blood is from a newborn human infant, including a premature human infant, or the blood is from a laboratory animal or even adult humans for epidemiological studies.

The enzyme assay may be used provide diagnostic information about an enzyme deficiency. For example, the enzyme deficiency may include one or more lysosomal storage diseases, such as Pompe, Niemann-Pick, Fabry, Hunter, Hurler, Maroteaux-Lamy, Krabbe, and Gaucher. Other lysosomal storage and glycogen storage diseases are described and/or listed herein. The method may include providing therapeutic treatment to a subject based on the screening and subsequent diagnostic information. In some cases, the enzyme assay is used to test enzymes from cultured cells and/or supernatant from a cell culture.

These and many other aspects of the invention will be apparent in the ensuing discussion.

DEFINITIONS

As used herein, the following terms have the meanings indicated.

"Activate" with reference to one or more electrodes means effecting a change in the electrical state of the one or more electrodes which, in the presence of a droplet, results in a droplet operation.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® particles, available from Invitrogen Corp., Carlsbad, Calif.), fluorescent microparticles and nanoparticles, coated magnetic microparticles and nanoparticles, ferromagnetic microparticles and nanoparticles, coated ferromagnetic microparticles and nanoparticles, and those described in U.S. Patent Publication No. 20050260686, entitled, "Multiplex flow assays preferably with magnetic particles as solid phase," published on Nov. 24, 2005, the entire disclosure of which is incorporated herein by reference for its teaching concerning magnetically responsive materials and beads. Beads may be pre-coupled with a biomolecule (ligand). The ligand may, for example, be an antibody, protein or antigen, DNA/RNA probe or any other molecule with an affinity for the desired target. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. Patent Application No. 61/039,183, entitled "Multiplexing Bead Detection in a Single Droplet," filed on Mar. 25, 2008; U.S. Patent Application No. 61/047,789, entitled "Droplet Actuator Devices and Droplet Operations Using Beads," filed on Apr. 25, 2008; U.S. Patent Application No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator. For examples of droplet fluids that may be subjected to droplet operations using the approach of the invention, see International Patent Application No. PCT/US 06/47486, entitled, "Droplet-Based Biochemistry," filed on Dec. 11, 2006. In various embodiments, a droplet may include a biological sample, such as whole blood, blood cells, chorionic villus cells, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. Other examples of droplet contents include reagents, such as a reagent for a biochemical protocol, such as a nucleic acid amplification protocol, an affinity-based assay protocol, an enzyme assay protocol, a sequencing protocol, and/or a protocol for analyses of biological fluids.

"Droplet Actuator" means a device for manipulating droplets. For examples of droplet actuators, see U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. Nos. 6,773,566, entitled "Electrostatic Actuators for Microfluidics and Methods for Using Same," issued on Aug. 10, 2004 and 6,565,727, entitled "Actuators for Microfluidics Without Moving Parts," issued on Jan. 24, 2000, both to Shenderov et al.; Pollack et al., International Patent Application No. PCT/US2006/047486, entitled "Droplet-Based Biochemistry," filed on Dec. 11, 2006; and Roux et al., U.S. Patent Pub. No. 20050179746, entitled "Device for Controlling the Displacement of a Drop Between two or Several Solid Substrates," published on Aug. 18, 2005; the disclosures of which are incorporated herein by reference. Certain droplet actuators will include a substrate, droplet operations electrodes associated with the substrate, one or more dielectric and/or hydrophobic layers atop the substrate and/or electrodes forming a droplet operations surface, and optionally, a top substrate separated from the droplet operations surface by a gap. One or more reference electrodes may be provided on the top and/or bottom substrates and/or in the gap. In various embodiments, the manipulation of droplets by a droplet actuator may be electrode mediated, e.g., electrowetting mediated or dielectrophoresis mediated or Coulombic force mediated. Examples of other methods of controlling fluid flow that may be used in the droplet actuators of the invention include devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and optoelectrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed in droplet actuators of the invention.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles.

"Filler fluid" means a fluid associated with a droplet operations substrate of a droplet actuator, which fluid is sufficiently immiscible with a droplet phase to render the droplet phase subject to electrode-mediated droplet operations. The filler fluid may, for example, be a low-viscosity oil, such as silicone oil. Other examples of filler fluids are provided in International Patent Application No. PCT/US2006/047486, entitled, "Droplet-Based Biochemistry," filed on Dec. 11, 2006; International Patent Application No. PCT/US2008/072604, entitled "Use of additives for enhancing droplet actuation," filed on Aug. 8, 2008; and U.S. Patent Publication No. 20080283414, entitled "Electrowetting Devices," filed on May 17, 2007; the entire disclosures of which are incorporated herein by reference. The filler fluid may fill the entire gap of the droplet actuator or may coat one or more surfaces of the droplet actuator. Filler fluid may be conductive or non-conductive.

"Immobilize" with respect to magnetically responsive beads, means that the beads are substantially restrained in position in a droplet or in filler fluid on a droplet actuator. For example, in one embodiment, immobilized beads are sufficiently restrained in position to permit execution of a splitting operation on a droplet, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, $CoO$, $NiO$, $Mn_2O_3$, $Cr_2O_3$, and $CoMnP$.

"Washing" with respect to washing a magnetically responsive bead means reducing the amount and/or concentration of one or more substances in contact with the magnetically responsive bead or exposed to the magnetically responsive bead from a droplet in contact with the magnetically responsive bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," granted on Oct. 21, 2008, the entire disclosure of which is incorporated herein by reference.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

DETAILED DESCRIPTION OF THE INVENTION

The invention relates to a microfluidic platform and methods of using the platform for conducting enzyme assays using a droplet actuator. The enzyme assays of the invention are useful for, among other things, identifying and/or characterizing disorders resulting from conditions in which enzymes are defective or are produced in inappropriate amounts. Enzyme assays of the invention may, for example, be used to detect altered activity of a particular enzyme in a sample, which may serve as an indicator of a particular disease. Altered activity may, for example, be caused by conditions which result in the increased or reduced production of a certain enzyme or its substrate and/or conditions which result in defective enzymes and/or substrates exhibiting increased or decreased effectiveness relative to corresponding normal enzymes and/or substrates.

In some cases, the enzyme assays of the invention are useful for screening inherited metabolic disorders, such as lysosomal storage diseases (LSD). In some embodiments, the microfluidic platform of the invention is configured for multiplexed detection of enzymatic disorders, such as lysosomal storage diseases (LSD). For example, in some cases, a single input sample, such as a blood droplet or a reconstituted blood droplet, may be loaded onto a droplet actuator of the invention, the sample may be dispensed into multiple sub-samples, and each of the sub-samples may be used to conduct an enzyme assay of the invention using droplet operations on the droplet actuator. In one embodiment, a single droplet actuator is configured to assay for 2, 3, 4, 5, 6, 7, 8, 9, 10, 20, 30, 40, 50 or more enzymatic conditions. In another embodiment, multiple samples from multiple subjects may be tested on a single droplet actuator for one or more conditions. In one embodiment, a single droplet actuator is configured to conduct assays using samples from 2, 3, 4, 5, 6, 7, 8, 9, 10, 20, 30, 40, 50 or more subjects.

The enzyme assays of the invention may have various advantages over conventional methods. As compared to the existing state of the art, the methods and platform of the invention may be used to conduct more assays per unit volume of sample. Small reaction volumes may permit assays to be completed more quickly, relative to existing techniques. The platform of the invention may be small and portable, facilitating testing in proximity to the subject, as compared to existing techniques which require shipment of samples to a central laboratory.

7.1 Droplet Actuator

In some cases, the assays of the invention are performed using a droplet actuator. A variety of droplet actuator layouts will be suitable.

Figure 1:
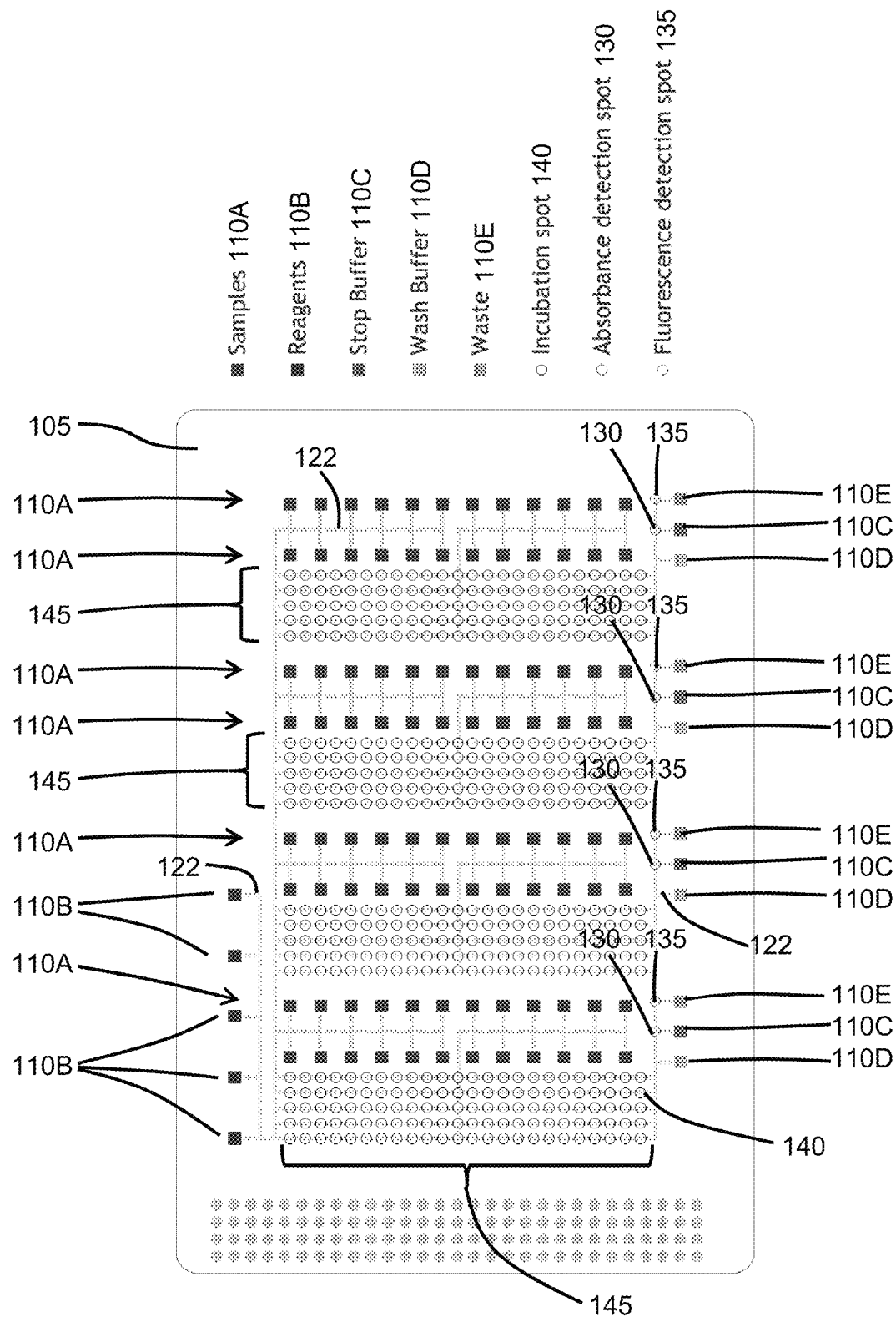
FIG. 1 provides an example of a droplet actuator layout for conducting enzyme assays.

FIG. 1 provides an example of a droplet actuator layout for conducting enzyme assays. The figure shows a bottom substrate 105 including a series of reservoirs 110. Reservoirs 110 may be allocated into sample reservoirs 110A, reagent reservoirs 110B, stop (quench) buffer reservoirs 110C, wash reservoirs 110D, and waste reservoirs 110E. Reservoirs 110 may be associated with openings in one or more substrates establishing fluid paths from a locus which is external to the droplet operations gap and extending into the droplet operations gap. For example, reservoirs 110 may be associated with openings in a top substrate (not shown) establishing a fluid path into the droplet operations gap. The openings may in some cases be associated with external reservoirs and/or in some cases the openings may be configured to receive a dispensing device, such as a pipette tip for dispensing fluid into the droplet actuator or a dried blood spot punch machine which would punch a spot into the reservoir. Reservoirs 110 are associated with an array 145 of droplet operations electrodes, which provide paths for dispensing, transporting, incubating and performing other droplet operations using droplets from reservoirs 110, and for bringing droplets into proximity with absorbance detection spots 130 and fluorescence detection spots 135. Array 145 of droplet operations electrodes (including individual incubation spots 140) also includes reaction/incubation areas for combining sample droplets with reagent droplets and for distributing and incubating reaction droplets. Paths 122 of electrodes are also provided as part of electrode array 145. Paths 122 provide droplet operations connection among reservoirs 110, absorbance detection spot 130, fluorescence detection spot 135, and incubation regions 145. Substrate 105 may be configured as a microtiter-plate (size and pitch) droplet actuator. Substrate 105 may be configured to set up 5-plex assays on 96 DBS samples (480 enzymatic assays). 96 sample droplets may be dispensed from sample reservoirs 110A and transported into and arrayed in incubation zone 145. 5 reagent reservoirs 110B distribute reagent droplets to each of 96 samples arranged one the droplet operations electrodes in 4 sets of 24. After incubation, each set of 120 droplets (24 samples×5 reagents) may be transported along the electrode array through an absorbance zone 130, combined using droplet operations with stop (quench) buffer droplet (dispensed from stop buffer reservoir 110C), and transported through a fluorescence detection zone 135, and to a waste reservoir 110E. The measurement of fluorescence may be used to quantify enzyme activity in the original sample. A user report may be generated by the system and provided to a user electronically and/or as a printed report.

In some high-throughput operations it may be useful to conform droplet actuators to conform to the SBS standard microtiter plate footprint and pitch, so that the droplet actuators will be compatible with existing robotic plate-handling equipment. In the embodiment illustrated in FIG. 1, each of the 24 reservoirs are set apart on a 4.5 mm grid (well-to-well pitch in a 384-well plate) so that a technician can easily load these reservoirs with DBS extracts from a 96-well plate by just using a multi-channel pipettor and laterally translating three times to load all the 96 sample reservoirs.

Figure 2:
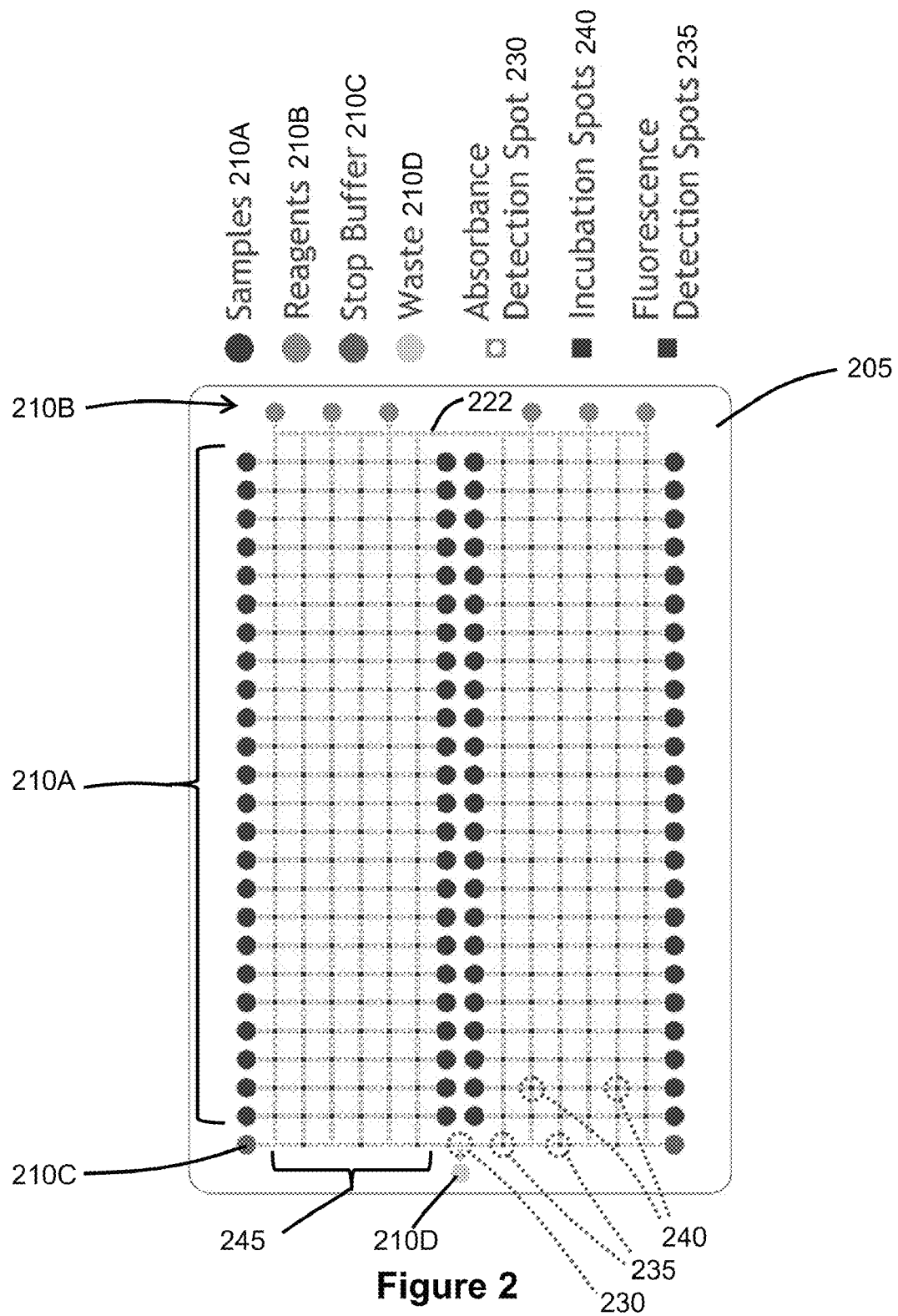
FIG. 2 shows another embodiment of a droplet actuator layout for conducting enzyme assays.

FIG. 2 shows another embodiment of a droplet actuator layout for conducting enzyme assays. The figure shows a bottom substrate 205 including a series of reservoirs 210. Reservoirs 210 may be allocated into sample reservoirs 210A, reagent reservoirs 210B, stop (quench) buffer reservoirs 210C, and waste reservoirs 210D. Reservoirs 210 may be associated with openings in one or more substrates establishing fluid paths from a locus which is external to the droplet operations gap and extending into the droplet operations gap. For example, reservoirs 210 may be associated with openings in a top substrate (not shown) establishing a fluid path into the droplet operations gap. The openings may in some cases be associated with external reservoirs and/or in some cases the openings may be configured to receive a dispensing device, such as a pipette tip for dispensing fluid into the droplet actuator or a dried blood spot punch machine which would punch a spot into the reservoir. Reservoirs 210 are associated with an array 245 of droplet operations electrodes, which provide paths for dispensing, transporting, incubating and performing other droplet operations using droplets from reservoirs 210, and for bringing droplets into proximity with absorbance detection spots 230 and fluorescence detection spots 235. Array 245 of droplet operations electrodes also includes reaction/incubation areas for combining sample droplets with reagent droplets and for distributing and incubating reaction droplets (e.g., on incubation spots 240). Paths 222 of electrodes are also provided as part of electrode array 245. Paths 222 provide droplet operations connection among reservoirs 210, absorbance detection spot 230, fluorescence detection spot 235, and incubation regions 245.

The droplet actuator architecture illustrated in FIG. 2 is configured for performing 6-plex enzymatic assays on 96 samples for a total of 576 enzymatic assays. The droplet actuator includes 96 sample inlets in sets of 24 reservoirs. Each of the 24 reservoirs is set apart in a 384-well plate pitch so that a technician can easily load these reservoirs with DBS extracts from a 96-well plate using a 8-channel pipettor and laterally translating three times to load each set of 24 wells out of the 96 sample reservoirs. The droplet actuator also includes reagent reservoirs (one reservoir for each respective 4-MU substrate), sample reservoirs 210A, a stop buffer reservoir 210C and waste reservoir 210D. A wash reservoir (not shown) may also be provided. For high throughput operation in a newborn screening setting, the droplet actuator design may be scaled to conform to the SBS standard microtiter plate footprint and pitch, so that the droplet actuators will be compatible with existing robotic plate-handling equipment. For example, in the embodiment shown, each reservoir is placed on a 4.5 mm grid (well-to-well pitch in a 384-well plate). The reservoirs 210 are connected together by a grid of electrodes capable of dispensing droplets from and to the reservoirs, transporting droplets to and from reservoirs 210 and detection zones, and incubating the 288 assays at one time. The droplet actuator is divided into 2 halves. Each half is identical to the other half. Each half has two sets of 24 sample reservoirs (total 48 reservoirs in each half), 3 reagent reservoirs and real-estate to park or incubate 24×6 reactions (144 simultaneous reactions in each half for a total of 288 reactions). The reagent reservoirs are connected by a common 'bus' which can be used to transport droplets from one half to the other or simply each half can have its own set of 6 reservoirs which means the technician has to load the reagents twice. Since there are only 144 incubation spots in each half, only 24 samples can be reacted with 6 substrates at any time. In each half, after the first set of 24 samples may be assayed, the next set of 24 samples is setup with its respective substrates. Therefore, two sets of reactions are conducted in series where each set of reaction contains 288 individual reactions. The architecture also has a dedicated area for detection using a multi-channel fluorimeter and a spot for measuring absorbance. This parallel architecture can readily be scaled to 384 reservoirs or larger by reducing the size of the electrodes and/or by increasing the size of the droplet actuator.

In operation sample droplets may be merged using droplet operations with their respective reagent droplets and set for incubation in the long vertical pathways which serve as incubation zones. After incubation, the droplets may be transported into proximity with the optical detectors, first through an absorbance zone and then to a fluorescence spot. A stop buffer droplet will be dispensed and mixed with each of the incubated droplets just before reaching the fluorescence spot. Reaction droplets may be trailed by one or more wash droplets to clean up the fluorescence detection spot of any potential left-over material. In the embodiment illustrated in FIG. 1, each set of 24 reservoirs has its own optical detection zones.

Droplet actuator systems may take on a wide variety of configurations. For the purpose of illustration only, one such configuration includes an electrical controller, which has a microprocessor and switching circuitry to control 108 high-voltage electrical I/Os. 8 digital I/O pins can be used for detecting the presence and unique identification of the cartridge to allow traceability back to manufacturing records. The electrical interface may include spring-loaded connector pins to make electrical contact with the droplet actuator. Controllers and software may be used to switch 108 high voltage channels independently. Impedance detection may be implemented in the controller hardware so that any microfluidic failures such as an unresponsive droplets can be detected, and other droplets can be routed around it. In some cases, firmware in the microprocessor on-board the instrument may be used to handle sequences for switching, detection, data capture, storage, and communication.

Typically, sample and reagent may be loaded through reservoirs associated with the droplet actuator. As noted, the reservoirs are ideally spaced apart in a 384-well plate pitch of 4.5 mm to make them compatible with existing punch devices and robotics. However, such spacing is not required. Reservoirs are typically sized to permit dispensing 10's to 1000's of droplets in the droplet operations gap without requiring refilling. Larger reservoirs are useful for holding and dispensing the stop buffer and wash buffer. Stop buffer may also be used as a wash buffer or as a blank for absorbance measurements. Lower capacity reservoirs may typically be used for samples (~6 droplets) and medium capacity reservoirs may typically be used for reagents (~96 droplets). Again, these dimensions are illustrative only, and it will be appreciated that changes in configuration will be apparent to the skilled artisan in light of this specification. For example, in a droplet actuator conducting a larger number of tests per subject, a larger sample reservoir may be provided. Examples of suitable reservoir arrangements are described in Pollack et al., International Patent Pub. No. WO/2008/124846, entitled "Droplet Dispensing Device and Methods," published on Oct. 16, 2008; and Srinivasan et al., International Patent Pub. No. WO/2009/032863, entitled "Droplet Actuator with Improved Top Substrate," published on Mar. 12, 2009; the entire disclosures of which are incorporated herein by reference. The top substrate may be made from any suitable material. Common examples include machined plastic and glass or injection molded plastic. The bottom substrate is commonly printed circuit board or a silicon chip including electrodes, wires and contact pads, though any material suitable for forming and wiring the electrodes may be used.

7.2 Sample

The enzyme assays of the invention make use of sample droplets and substrate droplets. Sample droplets are blood or blood-derived samples, such as plasma, serum, tissue, cell fractions, and treated, fractionated, concentrated and/or diluted forms of the foregoing. For example, diagnosis for Pompe disease is performed on fibroblasts. Other biological fluids may be used as samples; nonlimiting examples include tears, semen, urine, saliva, amniotic liquid and cerebrospinal fluid. For example, in the testing to diagnose Fabry disease, tears may be used as the input sample droplet. Still other examples of biological fluids are listed hereinbelow. Biological fluids may be treated as necessary to prepare them for being subjected to the protocols of the invention. For example, samples may be diluted or buffered, heated or cooled; pH may be adjusted; and/or blood samples may be treated with one or more anticoagulants. Samples may be loaded into a reservoir associated with a droplet actuator, and may be dispensed into one or more subsamples. In some cases, the subsamples are unit-sized subsamples. The subsamples may be in contact with or surrounded with one or more filler fluids.

In one embodiment, the sample includes a reconstituted dried blood spot. Typically the subject's skin is pricked using a sterile puncture device, such as a lancet. Droplets of blood are spotted onto filter paper and allowed to dry. The filter paper may, for example, be a Whatman Neonatal Screening Card, such as the Whatman 903 Neonatal Blood Collection Card (available from GE Healthcare, Inc.). To reconstitute the dried blood spots, a small disc is punched from the filter paper and placed in solution to yield a solution of reconstituted blood. The disc typically has a diameter of about 3.2 mm, though other sizes may be used. The reconstituted blood solution may be loaded onto a droplet actuator where it is subject to droplet operations for conducting one or more assays.

In some embodiments, the disc may be punched directly into a droplet actuator reservoir, such as a reservoir situated in a droplet operations gap and/or a reservoir which is external to the droplet operations gap. The external reservoir may be associated with a fluid passage suitable for flowing reconstituted blood sample into the droplet operations gap. Fluid input reservoirs may be sized to accommodate a punch and reconstitution solution. In one embodiment, the well-to-well pitch is 4.5 mm which is sufficient to fit a 3 mm DBS punch. Reservoirs may thus be arranged to permit use of existing punchers, such as the Perkin-Elmer DBS Puncher™. Since the inner surfaces of the droplet operations gap are hydrophobic, the reconstitution solution, when added in to the reservoir, will remain in the reservoir. Liquid from the reservoir containing the punch can be pulled into the droplet actuator through electric field to form droplets for subsequent enzymatic assays. Reservoirs may be associated with agitators or sonicators to effect mixing of the reconstituted samples. Any tendency of reconstituted sample to flow into the droplet operations gap, e.g., during moving or shaking of the droplet actuator, may be reduced or minimized by lowering the pressure of the liquid by configuring the reservoir to reduce the height of the liquid column in the reservoir.

In some embodiments, a disc having a diameter of less than about 8 mm is reconstituted in less than about 1000 µL of solution, the sample is dispensed into at least 10 sub-droplets, and each sub-droplet is used to conduct a different enzyme assay. In other embodiments, a disc having a diameter of less than about 4 mm is reconstituted in less than about 1000 µL of solution, the sample is dispensed into at least 10 sub-droplets, and each sub-droplet is used to conduct a different enzyme assay. In some embodiments, a disc having a diameter of less than about 8 mm is reconstituted in less than about 500 µL of solution, the sample is dispensed into at least 10 sub-droplets, and each sub-droplet is used to conduct a different enzyme assay. In other embodiments, a disc having a diameter of less than about 4 mm is reconstituted in less than about 500 µL of solution, the sample is dispensed into at least 10 sub-droplets, and each sub-droplet is used to conduct a different enzyme assay. In other embodiments, a disc having a diameter of less than about 8 mm is reconstituted in less than about 1000 µL of solution, the sample is dispensed into at least 20 sub-droplets, and each sub-droplet is used to conduct a different enzyme assay. In other embodiments, a disc having a diameter of less than about 4 mm is reconstituted in less than about 1000 µL of solution, the sample is dispensed into at least 20 sub-droplets, and each sub-droplet is used to conduct a different enzyme assay. In some embodiments, a disc having a diameter of less than about 8 mm is reconstituted in less than about 500 µL of solution, the sample is dispensed into at least 20 sub-droplets, and each sub-droplet is used to conduct a different enzyme assay. In some embodiments, a disc having a diameter of less than about 4 mm is reconstituted in less than about 500 µL of solution, the sample is dispensed into at least 20 sub-droplets, and each sub-droplet is used to conduct a different enzyme assay. In some embodiments, a disc having a diameter of less than about 8 mm is reconstituted in less than about 1000 µL of solution, the sample is dispensed into at least 100 sub-droplets, and each sub-droplet is used to conduct a different enzyme assay. In other embodiments, a disc having a diameter of less than about 4 mm is reconstituted in less than about 1000 µL of solution, the sample is dispensed into at least 100 sub-droplets, and each sub-droplet is used to conduct a different enzyme assay. In some embodiments, a disc having a diameter of less than about 8 mm is reconstituted in less than about 500 µL of solution, the sample is dispensed into at least 100 sub-droplets, and each sub-droplet is used to conduct a different enzyme assay. In some embodiments, a disc having a diameter of less than about 4 mm is reconstituted in less than about 500 µL of solution, the sample is dispensed into at least 100 sub-droplets, and each sub-droplet is used to conduct a different enzyme assay. In some embodiments, a disc having a diameter of less than about 8 mm is reconstituted in less than about 100 µL of solution, the sample is dispensed into at least 20 sub-droplets, and each sub-droplet is used to conduct a different enzyme assay. In some embodiments, a disc having a diameter of less than about 4 mm is reconstituted in less than about 100 µL of solution, the sample is dispensed into at least 20 sub-droplets, and each sub-droplet is used to conduct a different enzyme assay. In some embodiments, a disc having a diameter of less than about 8 mm is reconstituted in less than about 100 µL of solution, the sample is dispensed into at least 100 sub-droplets, and each sub-droplet is used to conduct a different enzyme assay. In some embodiments, a disc having a diameter of less than about 4 mm is reconstituted in less than about 100 µL of solution, the sample is dispensed into at least 100 sub-droplets, and each sub-droplet is used to conduct a different enzyme assay.

In some cases, the droplet including an enzyme of interest is prepared by reconstituting a dried blood spot disc having a diameter of less than about 3 mm in less than about 200 µL of solution. The sample may, for example, be dispensed into at least 10 sample droplets, and each sample droplet is used to conduct a different enzyme assay. In another embodiment, the disc has a diameter of less than about 3 mm; the disk is reconstituted in less than about 200 µL of solution; the sample is dispensed into at least 5 sub-droplets; and at least 5 sub-droplets are each used to conduct a different enzyme assay. In another embodiment, the disc has a diameter of less than about 6 mm; the disc is reconstituted in less than about 800 µL of solution; the sample is dispensed into at least 5 sub-droplets; and at least 5 sub-droplets are each used to conduct a different enzyme assay. In another embodiment, the disc has a diameter of less than about 6 mm; the disc is reconstituted in less than about 800 µL of solution; the sample is dispensed into at least 5 sub-droplets; and at least 5 sub-droplets are each used to conduct a different enzyme assay. In another embodiment, the disc has a diameter of less than about 3 mm; the disk is reconstituted in less than about 200 µL of solution; the sample is dispensed into at least 10 sub-droplets; and at least 10 sub-droplets are each used to conduct a different enzyme assay. In another embodiment, the disc has a diameter of less than about 6 mm; the disc is reconstituted in less than about 800 µL of solution; the sample is dispensed into at least 10 sub-droplets; and at least 10 sub-droplets are each used to conduct a different enzyme assay. In another embodiment, the disc has a diameter of less than about 6 mm; the disc is reconstituted in less than about 800 µL of solution; the sample is dispensed into at least 10 sub-droplets; and at least 10 sub-droplets are each used to conduct a different enzyme assay. In another embodiment, the disc has a diameter ranging from about 1 mm to about 6 mm; the disc is reconstituted in solution ranging from about 22 µL to about 800 µL; the sample is dispensed into at least 5 sub-droplets; and at least 5 sub-droplets are each used to conduct a different enzyme assay.

In some cases, the volume of each of the sample and substrate droplets used to conduct the enzyme assays of the invention may range from about 1 nL to about 1000 µL; or about 1 nL to about 1000 nL; or about 1 nL to about 500 nL; or about 1 nL to about 250 nL. Where a dried blood spot is used, the sample droplet is prepared by reconstituting a dried blood spot disc. In some cases, the disc has a diameter of less than about 10 mm and is reconstituted in less than about 1000 µL of solution; or less than about 750 µL of solution; or less than about 500 µL of solution; or less than about 250 µL of solution; or ranging from about 25 µL to about 750 µL; or ranging from about 25 µL to about 500 µL; or ranging from about 25 µL to about 250 µL; or ranging from about 25 µL to about 150 µL. In some cases, the sample is dispensed into at least 5 sample droplets; or at least 10 sample droplets; or at least 25 sample droplets; or at least 40 sample droplets. In some cases, the dried blood spot disc has a diameter ranging from about 1 mm to about 10 mm; or from about 1 mm to about 8 mm; or from about 1 mm to about 6 mm; or from about 1 mm to about 4 mm.

In another aspect of the invention, fresh blood from a subject is used to conduct the assays of the invention. In one aspect, less than about 1.0 mL of blood is removed from a newborn. In another aspect, less than about 0.1 mL of blood is removed from a newborn. In another aspect, less than about 0.05 mL of blood is removed from a newborn. In another aspect, less than about 0.01 mL of blood is removed from a newborn. The removed blood may be deposited into a reservoir on a droplet actuator. In some cases a diluents and/or buffer droplet may be combined with the fresh blood sample. In some cases a droplet comprising an anticoagulant may be combined with the fresh blood sample or an anticoagulant may be mixed with the sample droplet.

7.3 Substrate

The enzyme assays of the invention make use of substrate droplets. A substrate droplet typically includes a substrate for the enzyme being tested. In some cases, however, the enzyme may be provided in the substrate droplet, while the substrate is provided in the sample droplet. In the typical embodiment, the substrate droplet includes a substrate with a detectable element. The detectable element is an element that produces a detectable signal which is modified, i.e., increased, reduced, or otherwise altered, by the activity of the enzyme.

In one aspect of this embodiment, the detectable element is a fluorophore. Examples of suitable fluorophores include, 4-methylumbelliferyl. 4-methylumbelliferyl glycosides may be utilized as substrates in the glycosidase assays of the invention. 4-methylumbelliferyl may be coupled via an alpha or beta linkage to glucose, galactose, fucose, mannose, sialic acid, hexose, hexosamine, N-acetylated hexosamine and other saccharides. The appropriate 4-methylumbelliferyl glycoside may be used as the substrate for the appropriate enzyme. For example, 4-methylumbelliferyl α-D-glucopyranoside may be used as the substrate in an assay for analysis of the activity of α-glucosidase in a sample, as indicator of Pompe disease. Similarly, 4-methylumbelliferyl α-D-galactopyranoside may be used as the substrate in an assay to analyze the activity of α-galactosidase in a sample, as indicator of Fabry disease. Further, 4-methylumbelliferyl-2-sulfate-iduronic acid (4-MU-I-2SO$_4$) may be used as the substrate in an assay with L-iduronidase to analyze the activity of iduronate-2-sulfatase (I2S).

Examples of suitable substrates include, without limitation, the following: β-secretase substrate 5, Swedish Double Mutation Sequence [HiLyte Fluor™ 488-Glu-Val-Asn-Leu-Asp-Ala-Glu-Phe-Lys[QXL™ 520]-OH]; β-trifluoromethylumbelliferyl-β-D-galactopyranoside; β-trifluoromethylumbelliferyl-β-D-glucuronide; [Z-AA]2Rh110 [rhodamine 110, bis-[CBZ-L-alanyl-L-alanine amide]]; [Z-Ala-Ala-Ala-Ala]2Rh110 [rhodamine 110, bis-[CBZ-L-alanyl-L-alanyl-L-alanyl-L-alanine amide]]; [Z-AR]2Rh110.2HCl [rhodamine 110, bis-[CBZ-L-alanyl-L-arginine amide]]; [Z-Arg]2Rh110.2HCl [rhodamine 110, bis-[CBZ-L-arginine amide]]; 2',7'-dichlorodihydrofluorescein diacetate [H2DCFDA, H2DCF DA]; 3-cyano-7-ethoxycoumarin; 360 MMP FRET substrate I; 360 MMP FRET substrate II; 360 MMP FRET substrate III; 360 MMP FRET substrate IV; 360 MMP FRET substrate V; 360 MMP FRET substrate VI; 390 MMP FRET substrate I; 390 MMP FRET substrate II; 390

MMP FRET substrate II; 390 MMP FRET substrate III; 390 MMP FRET substrate IV; 4-CN [4-chloro-1-naphthol]; 4-methylumbelliferyl-β-D-glucoside; 4-nitrophenyl-α-D-galactopyranoside; 4-nitrophenyl-α-D-glucopyranoside; 4-nitrophenyl-α-D-mannopyranoside; 4-nitrophenyl-β-D-cellobioside; 4-nitrophenyl-β-D-fucopyranoside; 4-nitrophenyl-β-D-galactopyranoside; 4-nitrophenyl-β-D-glucopyranoside; 4-nitrophenyl-β-D-glucuronic acid; 4-nitrophenyl-N-acetyl-b-D-galactosaminide; 4-nitrophenyl-N-acetyl-b-D-glucosaminide; 490 MMP FRET substrate III; 490 MMP FRET substrate III; 490 MMP FRET substrate IV; 490 MMP FRET substrate V; 490 MMP FRET substrate VI; 490 MMP FRET substrate VII; 5-[and-6]-Carboxy-2',7'-dichlorodihydrofluorescein diacetate; 5-carboxy-2',7'-dichlorodihydrofluorescein diacetate, di[acetoxymethyl ester]; 5-FAM MMP FRET peptide fluorescence standard I; 520 MMP FRET substrate I; 520 MMP FRET substrate II; 520 MMP FRET substrate III; 520 MMP FRET substrate IV; 520 MMP FRET substrate IX; 520 MMP FRET substrate V; 520 MMP FRET substrate VI; 520 MMP FRET substrate VII; 520 MMP FRET substrate VIII; 520 MMP FRET substrate X; 520 MMP FRET substrate XI; 520 MMP FRET substrate XII; 520 MMP FRET substrate XIII; 520 MMP FRET substrate XIV; 520 MMP FRET substrate XV; 520 MMP FRET substrate XVI; 520 MMP FRET substrate XVII; 580 MMP FRET substrate I; 6-Carboxy-2',7'-dichlorodihydrofluorescin diacetate, di[acetoxymethyl ester]; 7-ethoxy-4-trifluoromethylcoumarin; Ac-IETD-ANARED™; ADHP [10-acetyl-3,7-dihydroxyphenoxazine]; AEC [3-amino-9-ethylcarbazole], 1M solution in DMSO; α-secretase substrate 1; BCIP [5-bromo-4-chloro-3-indoxyl phosphate, disodium salt]; benzyloxyresorufin [resorufin benzyl ether]; β-secretase substrate 1a; β-secretase substrate 2; β-secretase substrate 3, Swedish mutation sequence; casein, FITC conjugated; casein, TAMRA conjugated; caspase 1 [ICE] substrate 1m, fluorogenic [Ac-YEVD-AMC]; caspase 1 [ICE] substrate 2, chromogenic [Ac-YVAD-pNA]; caspase 1[ICE] substrate 2f, fluorogenic [Ac-YVAD-AFC]; caspase 1 [ICE] substrate 2m, fluorogenic [Ac-YVAD-AMC]; caspase 1 [ICE] substrate 2m, fluorogenic [Ac-YVAD-AMC]; caspase 1[ICE] substrate 2r, fluorogenic [Ac-YVAD]2-Rh110]; caspase 1 [ICE] substrate 3f, fluorogenic [Ac-WEHD-AFC]; caspase 1 [ICE] substrate 3r, fluorogenic [Ac-WEHD]2-Rh110]; caspase 2 [ICH-1] substrate 1, chromogenic [Ac-VDVAD-pNA]; caspase 2 [ICH-1] substrate 1f, fluorogenic [Ac-VDVAD-AFC]; caspase 2 [ICH-1] substrate 1m, fluorogenic [Ac-VDVAD-AM]C; caspase 2 substrate 3r [[D]2-Rh110]; caspase 2 substrate, chromogenic [Ac-VDQQD-pNA]; caspase 3 [apopain] substrate 1, chromogenic [Ac-DEVD-pNA]; caspase 3 [apopain] substrate 1f, fluorogenic [Ac-DEVD-AFC]; caspase 3 [apopain] substrate 1m, fluorogenic [Ac-DEVD-AMC]; caspase 3 [apopain] substrate 1r-z, fluorogenic [Z-DEVD]2-Rh110]; caspase 3 [apopain] substrate 1z, chromogenic [Z-DEVD-pNA]; caspase 3 [Apopain] substrate 2, chromogenic [Ac-DQMD-pNA]; caspase 3 substrate 1, chromogenic [Ac-DMQD-pNA]; caspase 3 substrate 1f, fluorogenic [Ac-DMQD-AFC]; caspase 3 substrate 1m, fluorogenic [Ac-DMQD-AMC]; caspase 3 substrate 1r, fluorogenic [Ac-DMQD]2-Rh110]; caspase 3 substrate, chromogenic [Ac-VQVD-pNA]; caspase 4 [ICH-2] substrate 1, chromogenic [Ac-LEVD-pNA]; caspase 4 [ICH-2] substrate 1f, fluorogenic [Ac-LEVD-AFC]; caspase 4 [ICH-2] substrate 1m, fluorogenic [Ac-LEVD-AMC]; caspase 4 [ICH-2] substrate 1r, fluorogenic [Ac-LEVD]2-Rh110]; caspase 6 [Mch2] substrate 1, chromogenic [Ac-VEID-pNA]; caspase 6 [Mch2] substrate 1f, fluorogenic [Ac-VEID-AFC]; caspase 6 [Mch2] substrate 1m, fluorogenic [Ac-VEID-AMC]; caspase 6 [Mch2] substrate 1r, fluorogenic [Ac-VEID]2-Rh110]; caspase 8 substrate 1, chromogenic [Ac-IETD-pNA]; caspase 8 substrate 1f, fluorogenic [Ac-IETD-AFC]; caspase 8 substrate 1m, fluorogenic [Ac-IETD-AMC]; caspase 8 substrate 1r-z, fluorogenic [Z-IEHD]2-Rh110]; caspase 9 substrate 1, chromogenic [Ac-LEHD-pNA]; caspase 9 substrate 1f, fluorogenic [Ac-LEHD-AFC]; caspase 9 substrate 1r, fluorogenic [Ac-LEHD]2-Rh110]; caspase 9 substrate 2m, fluorogenic [Ac-LEHD-AMC]; CMV protease FRET substrate I [DAB-CYL-Arg-Gly-Val-Val-Asn-Ala-Ser-Ser-Arg-Leu-Ala-EDANS]; collagen [Type I], FAM conjugated; collagen [Type I], FITC conjugated; collagen [Type IV], FAM conjugated; CUG [3-carboxyumbelliferyl-β-D-galactopyranoside]; D-ANARED™; D-luciferin, free acid; D-luciferin, potassium salt; D-luciferin, sodium salt; DAB NEW [3,3'-diaminobenzidine tetrahydrochloride]; dihydrocalcein, AM; dihydroethidium [hydroethidine]; dihydrofluorescein diacetate [H2FDA]; dihydrorhodamine 123; dihydrorhodamine 6G; elastin, FAM conjugated; elastin, FITC-conjugated; ethoxyresorufin [resorufin ethyl ether]; FDG [fluorescein di-β-D-galactopyranoside]; gelatin, FAM conjugated; HCV protease FRET substrate [RET S1]; HCV protease FRET substrate [RET S1]; HIV protease FRET substrate I; HPPA [3-[4-hydroxyphenyl]propionic acid]; luminol; malaria aspartyl proteinase FRET substrate I [DABCYL-Glu-Arg-Nle-Phe-Leu-Ser-Phe-Pro-EDANS]; Mca MMP FRET peptide fluorescence standard I; Mca MMP FRET peptide fluorescence standard II; methoxyresorufin [Resorufin methyl ether]; MMP biotinylated substrate I; MMP colorimetric substrate I; MMP HPLC substrate I; MMP HPLC substrate II; MMP HPLC substrate III; MMP Peptide Inhibitor I; MPTS [8-methoxypyrene-1,3,6-trisulfonic acid, trisodium salt]; MUG [4-methylumbelliferyl-β-D-galactopyranoside]; MUGlcU [4-methylumbelliferyl-β-D-glucuronide]; MUP [4-methylumbelliferyl phosphate, free acid]; MUP, DCA [4-methylumbelliferyl phosphate, dicyclohexylammonium salt, trihydrate]; MUP, DSS [4-methylumbelliferyl phosphate, disodium salt]; NBD methylhydrazine [N-methyl-4-hydrazino-7-nitrobenzofurazan]; NFF-2; NFF-2; NFF-3; NFF-3; pNPP [4-nitrophenyl phosphate, disodium salt]; renin FRET substrate I [DABCYL-g-Abu-Ile-His-Pro-Phe-His-Leu-Val-Ile-His-Thr-EDANS]; resazurin, sodium salt; resorufin β-D-Galactopyranoside; TACE FRET substrate I [DABCYL-Leu-Ala-Gln-Ala-Val-Arg-Ser-Ser-Ser-Arg-EDANS]; TACE FRET substrate I [DABCYL-Leu-Ala-Gln-Ala-Val-Arg-Ser-Ser-Ser-Arg-EDANS]; TMB [3,3",5,5"-tetramethylbenzidine dihydrochloride], 1M solution in DMSO; TNO113; TNO113; TNO211; TNO211; WAAG-3R, aggrecanase [ADAM-TS-4] FRET substrate; X-a-Gal [5-bromo-4-chloro-3-indolyl-α-D-galactopyranoside]; X-a-Glu [5-bromo-4-chloro-3-indoxyl-α-D-glucopyranoside]; X-b-xyloside [5-bromo-4-chloro-3-indoxyl-β-D-xylopyranoside]; X-fucoside [5-bromo-4-chloro-3-indoxyl-β-D-fucopyranoside]; X-Gal [5-bromo-4-chloro-3-indolyl-β-D-galactopyranoside]; X-GalNAc [5-bromo-4-chloro-3-indoxyl-N-acetyl-β-D-galactosaminide]; X-GlcU [5-bromo-4-chloro-3-indoxyl-β-D-glucuronic acid, sodium salt]; X-GluNAc [5-bromo-4-chloro-3-indoxyl-N-acetyl-β-D-glucosaminide]; X-InP [5-bromo-4-chloro-3-indoxyl myo-inositol-1-phosphate, ammonium salt]; Z-DEVD-AFC; Z-DEVD-AMC. These and other substrates are available from AnaSpec, Inc. (Fremont, Calif.). The substrates may be provided in substrate droplets of the invention.

In certain embodiments it is useful to remove contaminants from the substrate droplet, e.g., by photobleaching or otherwise purifying the droplet to remove contaminants prior to the assay reaction. The inventors have found that a reaction contaminant present in the 4-methylumbelliferyl preparation extends the time required for conducting the assay. Contaminant removal, e.g., by photobleaching of the reagent, appears to reduce or eliminate the impact of the reaction contaminant(s), resulting in reduced, preferably greatly reduced, reaction time. For example, the 4-methylumbelliferyl glycoside substrate may be photobleached prior to the assay reaction. For example, in some cases the photobleaching step decreases the reaction time from about 22 hours to about 30 minutes.

Reagent solution including substrate may be loaded into a reservoir associated with a droplet actuator, and may be dispensed into one or more sub-droplets. In some cases, the sub-droplets are unit-sized subsamples. The sub-droplets may be in contact with or surrounded with one or more filler fluids.

7.4 Quench Solution

In some cases, it may be helpful to quench the enzyme reaction prior to detection. Examples of quenching solutions include those which stop the enzyme reaction without causing undue damage to the droplet actuator or without causing undue interference with the signal. "Undue damage" in this context is damage that renders the droplet actuator unfit for its intended purpose. "Undue interference" in this context is interference which renders the signal unsuited for its intended purpose. Typical quenching droplets include acidic or alkaline droplets having a pH selected to quench the reaction without causing undue damage to the droplet actuator or without causing undue interference with the signal. Quenching may also be effected by temperature changes. For example, the droplet may be transported into a zone of the droplet actuator having a temperature selected to quench the reaction. In another example, the temperature of the droplet actuator may be adjusted to quench some or all reactions occurring thereon. In some cases, the termination buffer has an additional benefit of increasing the fluorescent signal of the product. Metalloenzymes may also be quenched or deactivated by the addition of a metal chelator such as EDTA or EGTA.

7.5 Enzyme Assays

The enzyme assays of the invention are accomplished using sample droplets and substrate droplets. A droplet actuator may be employed for conducting the assays using one or more droplet operations. Sample droplets and substrate droplets may be dispensed using droplet operations on a droplet actuator. Sample droplets and substrate droplets may be combined using droplet operations on a droplet actuator using droplet operations to yield one or more reaction droplets. Reaction droplets may be mixed using droplet operations on the droplet actuator. Reaction droplets may be incubated using droplet operations on the droplet actuator. Reaction droplets may be transported into a detection window and subjected to detection on a droplet actuator.

Various aspects of the invention are based on a series of surprising discoveries made by the inventors. Reagents (e.g., enzymes and substrates) required to effect enzyme assays may withstand the droplet operations conditions required for conducting enzyme assays on a droplet actuator. Reagents may be subjected to droplet operations in which the droplets are in contact with an immiscible filler fluid. The reactions may be conducted under such conditions using tiny reaction volumes, which are only a fraction of the reaction volumes used in currently available techniques, while still producing sufficient signal to provide accurate results. Signals from such droplets may be generated and reliably detected even in the presence of the filler fluid. Signals may be reliably detected even in embodiments in which they must travel through the reaction droplet, through one or more layers of filler fluid, and through a droplet actuator substrate, such as a transparent top substrate or a transparent detection window in a top substrate. The tiny volumes of sample and reagent used in the reactions of the invention may also enhance the speed of enzyme assays, allowing them to be conducted in a fraction of the time required using conventional methods.

The enzyme assays of the invention may be combined with other assay types. For example, an enzyme assay may be conducted on a sample for a certain disorder, and depending on the outcome of the enzyme assay, further assays, such as immunoassays, may be conducted to confirm or contradict the finding from the enzyme assay. In one example, an enzyme assay may be conducted on a sample for a certain metabolic disorder, and where results indicate a level of risk within a predetermined range, genetic material from the same sample source may be subjected to a PCR and/or nucleic acid sequencing protocol to confirm or deny the outcome from the enzyme assay. In some cases, the enzyme assay and genetic assay may be performed on the same droplet actuator. In other cases, a system may be programmed to load sample and conduct the genetic assay on a separate droplet actuator depending on the outcome of the enzyme assay.

In the assays of the invention, sample droplets and substrate droplets for use in conducting the enzyme assays may be dispensed and/or combined according to appropriate assay protocols using droplet operations on a droplet actuator. Incubation of assay droplets, including temperature adjustments as needed, may also be performed on a droplet actuator. Detection of signals from assay droplets, such as detection of fluorescence, may be conducted while the droplet is present on the droplet actuator. The droplet operations and detection steps may be conducted while the droplet is partially or completely surrounded by a filler fluid on the droplet actuator.

In certain embodiments, certain assay steps may be conducted outside of a droplet actuator and certain assay steps may be conducted on a droplet actuator. For example, in some embodiments, sample and reagents may be combined outside the droplet actuator and an incubation and detection steps may be effected on the droplet actuator. In other embodiments, certain assay steps may be performed using droplet operations on the droplet actuator, and reaction droplets may be removed from the droplet actuator for conducting certain additional steps, such as detection.

In certain embodiments, assay droplets may be combined with one or more buffer droplets, acidic droplets and/or basic droplets, in order to achieve a desired pH for conducting the enzyme assay of the invention. The enzyme assays are generally conducted at neutral to acidic pH. Some of the enzymatic assays described in the substrate section are performed at alkaline pH.

In one example, droplet operations may be utilized to combine on a droplet actuator the substrate droplet with a sample droplet. The droplets are provided at an appropriate pH, and the pH may be adjusted as needed by combining the sample, substrate, and/or sample+substrate droplets with appropriate buffer droplets. The sample+substrate droplet may then be incubated on the droplet actuator. The release of fluorophore, such as 4-methylumbelliferyl, in the droplet or the increase in fluorescence in the droplet versus time, may be measured. The measurement may take place while the droplet is on the droplet actuator, or alternatively, the droplet may be removed from the droplet actuator for the detection step. A user output may be produced showing results of the assay. Multiple assays may be conducted simultaneously in a single droplet, e.g., using different fluorophores for each enzyme tested.

The invention provides modified assays for detecting altered enzymatic activity. Among the enzyme assays which may be conducted according to the methods of the invention are those methods useful in the diagnosis of defects in glycosidases, such as lysosomal storage diseases. Enzymatic indicators of lysosomal storage diseases can be identified using droplet based assays on a droplet actuator. Assays of the appropriate glycosidase activity can be used to detect altered activity of a particular glycosidase, which may be an indicator of a particular lysosomal storage disease. A deficiency in α-glucosidase activity, for example, is a diagnostic indicator of Pompe disease. Similarly, a deficiency in α-galactosidase activity is a diagnostic indicator of Fabry disease. Multiple diseases and/or multiple samples can be tested simultaneously on a single droplet actuator.

In some embodiments, the invention provides diagnostic techniques for metabolic disorders that result from defects in lysosomal function. Examples include, without limitation: activator deficiency/GM2 gangliosidosis; alpha-mannosidosis; aspartylglucosaminuria; cholesteryl ester storage disease; chronic hexosaminidase a deficiency; cystinosis; Danon disease; Fabry disease; Farber disease; fucosidosis; galactosialidosis; Gaucher disease (Type I, Type II, Type III); GM1 gangliosidosis (infantile, late infantile/juvenile, adult/chronic); I-cell disease/mucolipidosis II; infantile free sialic acid storage disease/ISSD; juvenile hexosaminidase A deficiency; Krabbe disease (infantile onset, late onset); metachromatic leukodystrophy; mucopolysaccharidoses disorders (pseudo-hurler polydystrophy/mucolipidosis IIIA, PSI Hurler syndrome, MPSI Scheie syndrome, MPS I Hurler-Scheie syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio type A/MPS IVA, morquio Type B/MPS IVB, MPS IX hyaluronidase deficiency, MPS VI Maroteaux-Lamy, MPS VII Sly syndrome, mucolipidosis I/Sialidosis, mucolipidosis IIIC, mucolipidosis type IV); Maroteaux-Lamy; multiple sulfatase deficiency; Niemann-Pick disease (Type A, Type B, Type C); Neuronal ceroid lipofuscinoses (CLN6 disease—Atypical late infantile, late onset variant, early juvenile, Batten-Spielmeyer-Vogt/juvenile NCL/CLN3 disease, Finnish variant late infantile CLN5, Jansky-Bielschowsky disease/late infantile CLN2/TPP1 disease, Kufs/adult-onset NCL/CLN4 disease, northern epilepsy/variant late infantile CLN8, Santavuori-Haltia/infantile CLN1/PPT disease, beta-mannosidosis); Pompe disease/glycogen storage disease type II; Pycnodysostosis; Sandhoff disease/GM2 gangliosidosis (Adult Onset, Infantile, Juvenile); Schindler disease; Salla disease/sialic acid storage disease; Tay-Sachs/GM2 gangliosidosis; and Wolman disease. In one embodiment, the droplet actuator and/or method of the invention is set up and or executed to assess 1, 2, 3, 4, 5, 6, 7, 8, 9, 10, 20, 30, 40 or more of the foregoing conditions. In one embodiment, the droplet actuator and/or method of the invention is set up and or executed to assess 2, 3, 4, 5 or more of the following conditions Pompe (α-D-Glucosidase); Niemann-Pick (acid sphingomyelinase); Fabry (α-Galactosidase); Krabbe (galactocerebroside-β-galactosidase); Hunter; Hurler; Maroteaux-Lamy; and Gaucher (glucocerebroside-β-D-glucosidase). Various enzyme-related conditions, including without limitation lysosomal storage diseases, are described in the *Merck Manual*, 18 ed., Apr. 7, 2006, the entire disclosure of which is incorporated herein by reference.

In another embodiment, the methods of the invention are used to conduct enzyme tests for one or more of the following enzymes: acetyl-CoA-glucosaminide N-acetyltransferase; ADP-ribose protein hydrolase; amyloglucosidase; arylsulfatase A; branching enzyme; cathepsin K; ceramidase; cystinosin (lysosomal cystine transporter); debrancher enzyme (amyloglucosidase and oligoglucanotransferase); dolichol-PGlc: Man9GlcNAc2-PP-dolichol glucosyltransferase; dolichol-Pman: man5GlcNAc2-PP-dolichol mannosyltransferase; dolichol-P-mannose synthase; dolichyl-P-glucose: Glc-1-Man-9-GlcNAc-2-PPdolichyl-α-3-glucosyltransferase; epididymal secretory protein 1 (HE1; NPC2 protein); fructose 1,6-diphosphatase; galactosamine-6-sulfate sulfatase; galactosylceramide β-galactosidase; ganglioside β-galactosidase; GDP-fucose transporter-1; glucose transporter-2; glucose-6-phosphatase; glucose-6-phosphate translocase; glucosidase I; glucosylceraminde β-glucosidase; glycogen synthase; GM2 activator protein; heparan-S-sulfate sulfaminidase; hyaluronidase; iduronate sulfate sulfatase; liver and muscle phosphorylase kinase; liver phosphorylase; liver phosphorylase kinase; lysosomal acid lipase; lysosomal acid α-glucosidase; lysosomal membrane protein-2; lysosomal pepstatininsensitive peptidase; lysosomal transmembrane CLN3 protein; lysosomal transmembrane CLN5 protein; mannosephosphate isomeerase; mannosyl-α-1,6-glycoprotein-β-1,2-N-acetylglucosminyltransferase; metalloproteinase-2; microsomal glucose transporter; microsomal phosphate or pyrophosphate transporter; muscle phosphorylase; muscle phosphorylase kinase; Na phosphate cotransporter; Na phosphate cotransporter; N-acetyl galactosamine α-4-sulfate sulfatase (arylsulfatase B); N-acetyl-Dglucosaminidase; N-acetyl-galactosaminidase; N-acetylglucosaminine-6-sulfate sulfatase; N-acetylglucosaminyl-1-phosphotransfeerase; N-acetylglucosaminyl-1-phosphotransfeerase catalytic subunit; N-aspartylglucosaminidase; neuraminidase 1 (sialidase); NPC1 protein; oligoglucanotransferase; oligomeric Golgi complex-7; palmitoyl-protein thioesterase-1; palmitoyl-protein thioesterase-1; phosphoenolpyruvate carboxykinase; phosphofructokinase; phosphomannomutase-2; prosaposin; protective protein/cathepsin A (PPCA); protein involved in mannose-P-dolichol utilization; Saposin B; Saposin C; sphingomyelinase; sterol 27-hydroxylase; sulfatase-modifying factor-1; transmembrane CLN6 protein; transmembrane CLN8 protein; trihexosylceramide α-galactosidase; UDPGlcNAc: dolichyl-P NAcGlc phosphotransferase; UDP-N-acetylglucosamine-2-epimerase/N-cetylmannosamine kinase; X-linked phosphorylase kinase; α-1,2-mannosyltransferase; α-1,3-mannosyltransferase; α-D-mannosidase; α-L-fucosidase; α-L-Iduronidase; β-1,4-galactosyltransferase; β-1,4-mannosyltransferase; β-D-mannosidosis; β-galactosidase; β-glucuronidase; β-hexosaminidase A; β-hexosaminidase A; and β-hexosaminidase B. In one embodiment, the droplet actuator and/or method of the invention is set up and or executed to assess 1, 2, 3, 4, 5, 6, 7, 8, 9, 10, 20, 30, 40 or more of the foregoing enzymes. The enzymes may be tested in one or more biological liquids, such as a blood sample, e.g., a reconstituted dried blood spot sample.

Enzyme assays for detecting such conditions may be accomplished in a much shorter time period as compared to assays conducted using conventional methods. For example, in certain embodiments, the incubation time required to effect diagnostically relevant results is less than about 20, 15, 10, 5, 4, 3, 2 or 1 hours. In certain other embodiments, the incubation time required to effect diagnostically relevant results is less than about 45, 30, 15, 10, 5, 4, 3, 2 or 1 minutes. Similarly, in certain embodiments, the incubation time required to effect diagnostically relevant results for lysosomal storage diseases involving defects in glycosidases is less than about 20, 15, 10, 5, 4, 3, 2 or 1 hours. In certain other embodiments, the incubation time required to effect diagnostically relevant results for lysosomal storage diseases involving defects in glycosidases is less than about 45, 30, 15, 10, 5, 4, 3, 2 or 1 minutes.

In one embodiment, a blank is formed by using droplet operations to split the reaction droplet into two droplets, combining the reaction droplet with a termination buffer to one, and immediately measuring the fluorescence of the droplet to get zero time point value. The zero time point value is subtracted from the fluorescent signal from the second droplet at a later time point to obtain the enzyme activity in the sample. In an alternative embodiment the substrate droplet is dispensed but not merged with a sample droplet. At the end of the incubation time, a sample droplet (the sample could be reconstituted from a DBS spotted with blood or it could comprise a blank DBS; in the latter case, only one zero assay would need to be run as opposed to one reaction per each blood spot DBS sample) and a termination buffer droplet are merged with the assay mix, and the fluorescence signal of the sample is measured. This method for determining the zero control accounts for non-enzymatic hydrolysis of the substrate and keeps the signal quenching materials from the sample constant between zero control and the sample. In a typical run, at least one reservoir out of every n sample reservoirs may be reserved for the zero and other controls. Hemoglobin content can vary widely between samples and may affect the reported value for the assays. As noted elsewhere herein, the method of the invention may include measuring the amount of hemoglobin in each droplet, e.g., using an absorbance method. The data collected from this measurement can be used to normalize the reported enzyme activities to a fixed hemoglobin value.

7.6 Detection

The methods of the invention include using one or more sensors for measuring droplet properties associated with the enzymatic reaction, such as physical properties, chemical properties, and electrical properties. In some embodiments, the method will include using a sensing element to detect a signal from a droplet; using a transducing element to convert output from the sensor into a signal; and transmitting the signal to a processor for analysis. The processor may convert the signal into an output recognizable to a user. The sensor element may be a component of the droplet actuator, e.g., mounted on a top or bottom substrate, positioned in the droplet operations gap, or manufactured as an integral component of the droplet actuator, e.g., an integral component of top or bottom substrates. In some embodiments, the sensor element may be exterior to the droplet actuator but arranged within the system in a manner which permits the sensor to receive a signal from on the droplet actuator, e.g., from a droplet on a droplet actuator. For example, a sensor element for sensing photons may be arranged to receive photons from a droplet on a droplet actuator. Where the system has a substrate capable of transmitting photons from a droplet, the sensor may be arranged in proximity to the substrate for sensing the photons. Where the system has a substrate not capable of transmitting photons from a droplet, the substrate may be provided with a detection window capable of transmitting photons, and the sensor may be arranged in proximity to the window for sensing the photons.

The droplet actuator and methods of the invention may make use of optical detectors. A droplet actuator and/or system of the invention may include one or more optical sensors arranged to sense a property of a droplet on a droplet actuator. Examples of optical sensing include absorbance, chemiluminescence, and fluorescence. Optical sensors may in some cases be accompanied with an appropriate light source, e.g., for exciting fluorescence or conducting absorbance measurements. These sensors may be provided as components mounted on a droplet actuator and/or as integral parts of a droplet actuator, e.g., using semiconductor manufacturing techniques.

Optical sensors may include various optics designed to direct optical signals, and may be coupled to various image processors for analyzing optical images. In some cases, surfaces of the droplet actuator may be modified to enhance optical sensing. For example, electrodes with reflective surface finishes may be used to facilitate optical measurements of droplets. The use of reflective electrodes increases the path length for absorbance measurements and is also compatible with reflectance spectroscopy. For auto-fluorescent substrates, such as PCB, coating a droplet actuator surface with a non-fluorescent coating can be used to provide a non-fluorescent detection zone or time resolved fluorophores could be used which will obviate the need for emission and excitation filters, and dichroic mirrors.

The droplet actuator device or system may include absorbance detection components including a light source and a photosensor arranged to permit a droplet on the droplet actuator to be transported into proximity with the light source and photosensor such that light or energy passing through the droplet can be detected by the photosensor.

The droplet actuator device or system may include chemiluminescence detection components including a photosensor (such as a photodiode, avalanche photodiode, photomultiplier tube) or photon sensor (such as a photon-counting photomultiplier tube) arranged to permit a droplet on the droplet actuator to be transported into proximity with the photosensor or photon sensor such that photons emitted by chemical species in the droplet can be detected by the photosensor or photon sensor.

The droplet actuator device or system may include fluorescence detection components including a light excitation source with appropriate filters, if necessary, and a photosensor (such as a photodiode, avalanche photodiode, photomultiplier tube) or a photon sensor (such as a photon-counting photomultiplier tube) with appropriate filters and dichroic mirrors, if necessary, arranged to permit a droplet on the droplet actuator to be transported into proximity with the light excitation source and the photosensor or photon sensor such that photons emitted by fluorescent species in the droplet can be detected by the photosensor or photon sensor.

In some embodiments, detection may be conducted at an assay endpoint. In other embodiments, kinetic assays may be employed in which the signal produced by the enzyme reaction is sampled or measured over time. For example, during a reaction, the signal produced by the enzyme reaction is sampled or measured 2, 3, 4, 5, 6, 7, 8, 9, 10, 20, 30, 40, 50, 100 or more times during the reaction in order to generate a reaction curve. In still other embodiments, a hybrid assay may be conducted in which a sample droplet is divided into a series of sub-droplets, each sub-droplet is combined with a substrate droplet to yield a reaction droplet, each reaction droplet is incubated for a different time period followed by an endpoint measurement, and the collective endpoint measurements are used to generate a curve. The resulting curve may be used to calculate enzyme activity in the sample. The sample may, for example, be dispensed and/or split into a series of 2, 3, 4, 5, 6, 7, 8, 9, 10 or more sub-droplets, each sub-droplet being incubated for a different time period. In yet another embodiment, a measurement is taken at the beginning and at the end of the reaction.

In some cases, incubation is effected at a first pH, while detection is effected at a different pH. In these embodiments, the reaction droplet may be combined using droplet operations with one or more buffer, acid and/or base droplets in order to adjust pH of the droplet to the appropriate pH for detection. In the hybrid assay described above, each reaction droplet may be incubated for a different time period followed by a pH adjustment and then an endpoint measurement. The collective endpoint measurements are used to generate a curve. It should also be noted that in reactions in which the pH changes during the reaction, it may be helpful add one or more buffer, acid and/or base droplets to the reaction order to adjust pH of the droplet to pH suitable for continuing the reaction.

Figure 3:
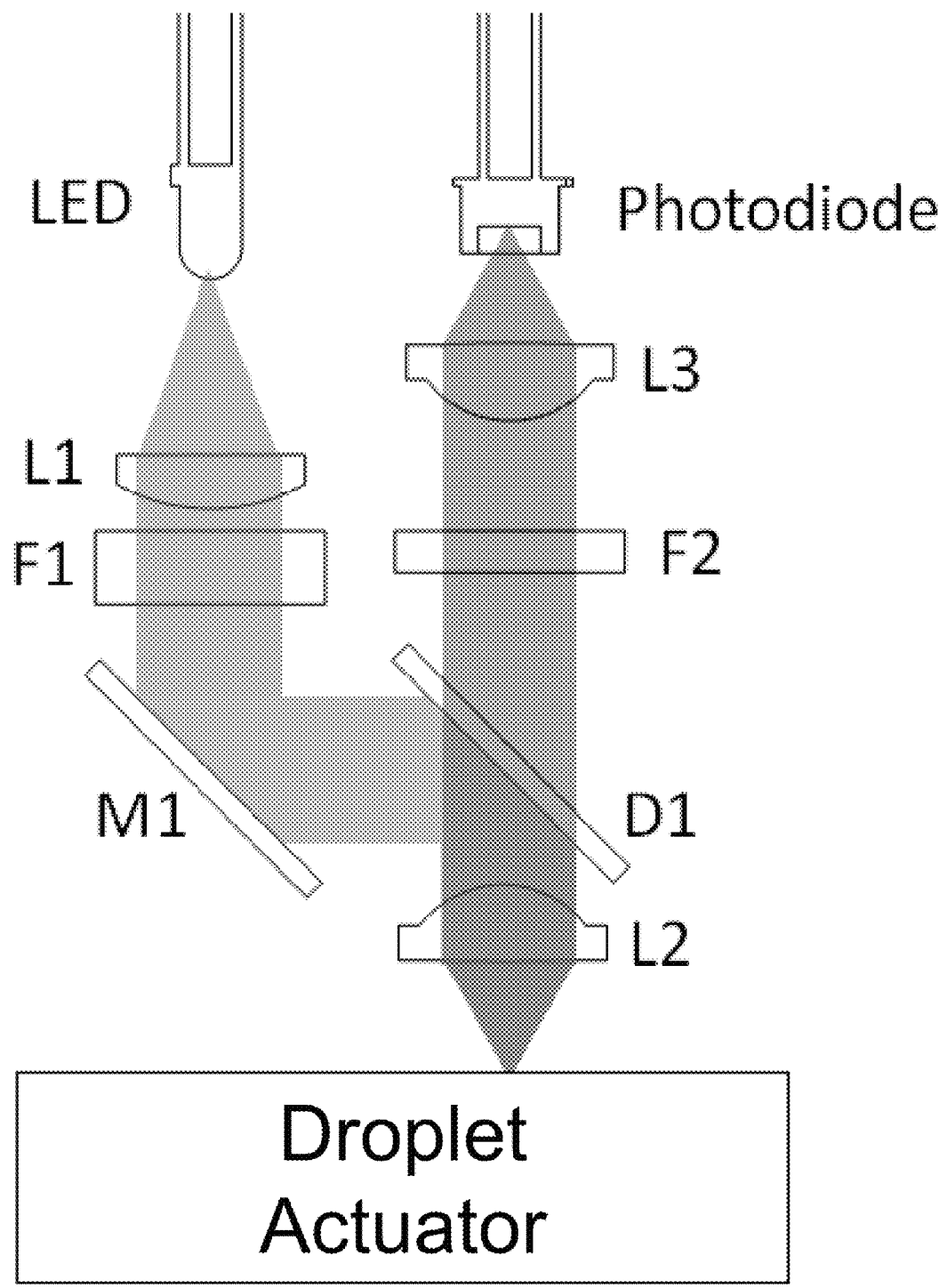
FIG. 3 illustrates an embodiment in which fluorescence emitted from a droplet actuator is measured by a single channel UV fluorimeter.

FIG. 3 illustrates an embodiment in which fluorescence emitted from a droplet actuator is measured by a single channel UV fluorimeter. Optically, the system includes a Nichia UV LED (375 nm) and a Hamamatsu photodiode arranged in an epi-illumination format. The UV LED light is collimated through lens L1, filtered through F1, reflected through mirror, M1, and dichroic D1, and finally focused by L2 to the sample. The fluorescence light from the sample is then collimated by the same lens, L2, passes through the dichroic mirror, D1, and is detected by a photodiode after being filtered by an emitter filter F2 and focused by lens, L3. The signal from the photodiode is immediately amplified by a transimpedance amplifier circuit. In order to reduce the contribution from ambient light and minimize overall noise, a lock-in circuit is employed. In some embodiments, multiple fluorimeters may be used to measure fluorescence from multiple droplets simultaneously.

Figure 4:
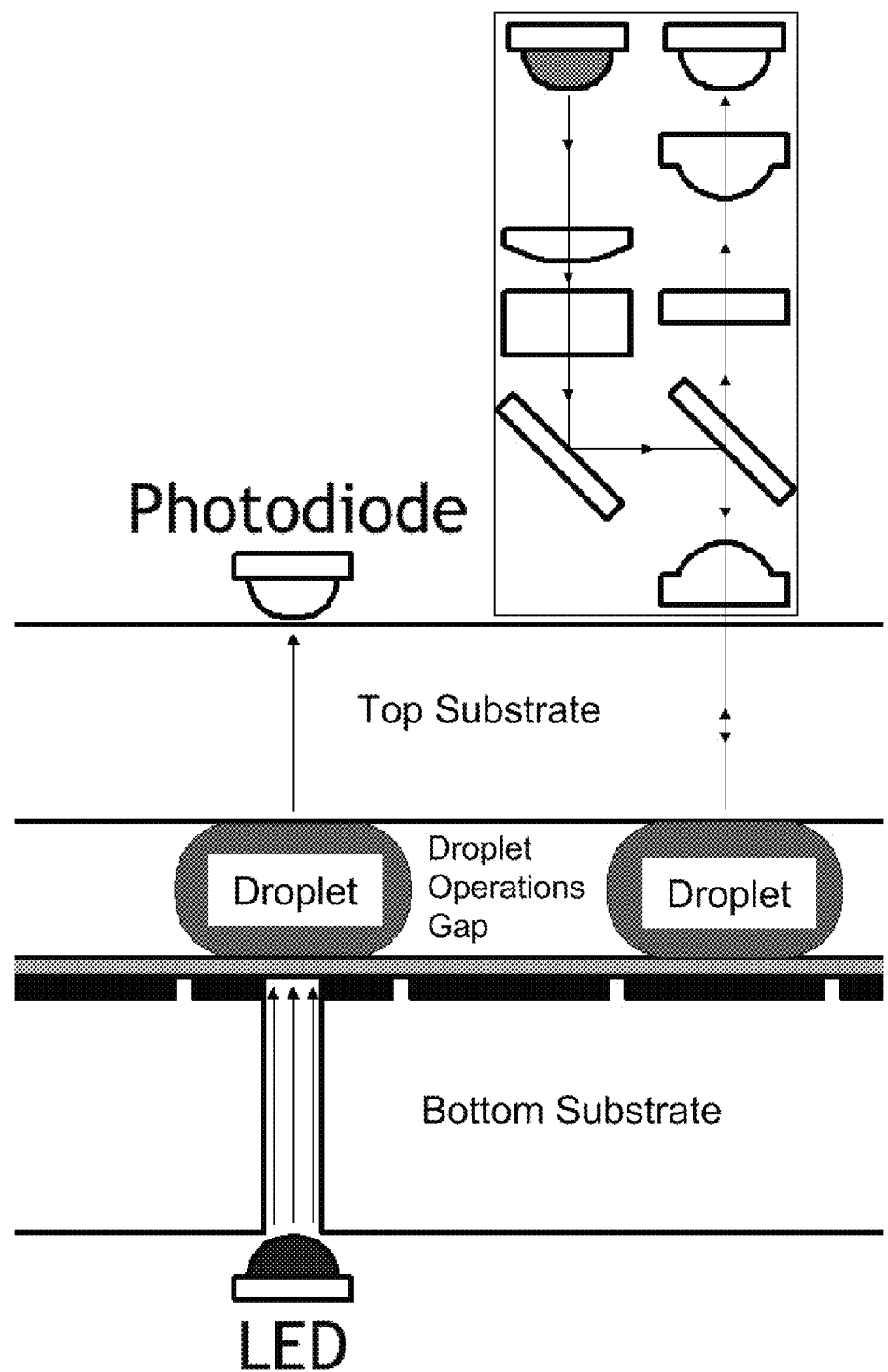
FIG. 4 illustrates an example of an absorbance setup, which may be included for measuring hemoglobin content of each sample droplet.

FIG. 4 illustrates an example of an absorbance setup, which may be included for measuring hemoglobin content of each sample droplet. Assayed droplets may be transported through the detection zone. In practice, for end point detection each droplet typically requires a residence time of about 2 seconds at the detector, with the total time for detection of 480 droplets with 4 detectors adding up to 4 minutes. In some cases, the absorbance setup for measurement of hemoglobin may include an LED at 405 nm for incident light and a photodiode. The incident source of light may be coupled through an optical fiber into the droplet actuator carrier board so that when a droplet actuator is inserted to make electrical contacts, the light source and detector will be automatically aligned to the transparent absorbance detection spot on the droplet actuator. Blank values for absorbance measurements may be taken from a stop buffer droplet before each DBS sample droplet passes through. In some cases, avalanche photodiodes may be used in place of regular photodiodes. Filters may be used to reduce background fluorescence.

7.7 Pompe Disease

Pompe disease is described here as a non-limiting example of an enzyme deficiency that may be assayed in accordance with the methods and devices of the invention. The disease is caused by a deficiency in the enzyme acid α-glucosidase, which is needed to metabolize glycogen. The invention provides a method of assessing acid α-glucosidase activity in a sample. Generally speaking, a droplet actuator is provided with a sample droplet and a droplet including a substrate with a detectable element, such as a fluorogenic substrate for detecting α-glucosidase. Sample and substrate may be loaded into on-actuator or off-actuator reservoirs for droplet operations dispensing of droplets into a droplet operations gap or onto a droplet operations surface. A sample droplet and a substrate droplet may be combined using droplet operations to produce a signal. The reaction droplet may be provided at, and/or adjusted to, an appropriate pH and incubated. Typical incubation time may, for example, be between about 30 minutes and about 22 hours for assays performed on DBS extracts and between 10 seconds and 1 hour for rate kinetic reactions performed on whole blood. When sufficient signal is generated, the reaction may be quenched by adding an alkaline droplet to the reaction droplet. The signal can be detected. An output can be generated showing results of the assay.

In one example, a dried blood spot is reconstituted in about 180 μL of reconstitution buffer to yield reconstituted blood sample. The reconstituted blood sample is loaded into a droplet actuator reservoir. On the droplet actuator, a sub-droplet of the reconstituted blood sample is dispensed and combined with one or more reagent droplets to yield a reaction droplet having a final concentration of about 1.4 mM 4-methylumbelliferyl α-D-glucopyranoside in about 0.04 M NaAc, pH 3.8 or pH 7.0, with or without about 5.9 μM of the inhibitor acarbose. The reaction droplet may be quenched with a droplet comprising $NaHCO_3$, pH≧~8, or pH≧~8.5, or pH≧~9.

7.7.1 Bench Assay of α-Glucosidase Activity

Table 1 shows the results of an assay of α-glucosidase activity for detecting Pompe disease. Table 1 shows fluorescence detected for blood+substrate, blood+substrate+inhibitor, and substrate+inhibitor, at pH 3.8 or pH 7.0. The assay is a bench-top assay, i.e., it is not conducted on a droplet actuator. The samples are assayed as described above. Here, blood is taken to mean extract from a dried blood spot.

TABLE 1

| Assay results of α-glucosidase activity for detecting Pompe disease (On-bench) | | |
|---|---|---|
|  | pH 3.8 | pH 7.0 |
| Blood + Substrate | 17813 | 11257 |
| Blood + Substrate + Inhibitor | 10898 | 4382 |
| Substrate + Inhibitor | 3214 | 3396 |

Samples were incubated for about 18 hours at about 25° C. The sample/reagent volume was about 2.5 μL. The reaction was quenched with about 100 μL of 0.1M $NaHCO_3$, pH 9.0. The fluorescence was detected on a substrate reader, measuring the wavelength 360 Ex/460 Em. As shown in Table 1, the signal was increased in the presence of substrate that has blood. The signal is decreased in the presence of the acarbose inhibitor which inhibits glycosidase activity.

7.7.2 Bench+Droplet Actuator Assay of α-Glucosidase Activity

Table 2 provides the results of a 4-methylumbelliferyl-α-D-glucopyranoside (MUG) assay of α-glucosidase activity to detect Pompe disease, indicating the amount of fluorescence detected for blood+MUG, blood+MUG+inhibitor, and water+MUG+inhibitor at pH 3.8 or pH 7.0. Incubation and quenching were conducted off the droplet actuator (off-actuator), and the reaction droplet was loaded onto the droplet actuator (on-actuator) for detection.

TABLE 2

| Assay results of α-glucosidase activity for detecting Pompe disease (Off-actuator incubation; On-actuator quench) | | |
|---|---|---|
|  | pH 3.8 | pH 7.0 |
| Blood + MUG | 89.8 | 76.4 |
| Blood + MUG + Inhibitor | 68.8 | 59.8 |
| Water + MUG + Inhibitor | 62.4 | 39.5 |

Referring to Table 2, the reactions were conducted in microfuge tubes, incubated for about 21.5 hours at about 25° C., and $NaHCO_3$ was added to quench the sample. A portion of the sample was removed and loaded onto the droplet actuator for the detection of fluorescence. The sample droplet was transported using droplet operations into the presence of the detector. An increase in fluorescence is observed in the presence of blood under all of the assay conditions (pH 3.8, pH 7.0) and in the presence or absence of inhibitor. The amount of fluorescence in the absence of inhibitor was greater than in the presence of inhibitor. Fluorescence in Table 2 is indicated by relative fluorescence units (RFU).

Figure 5:
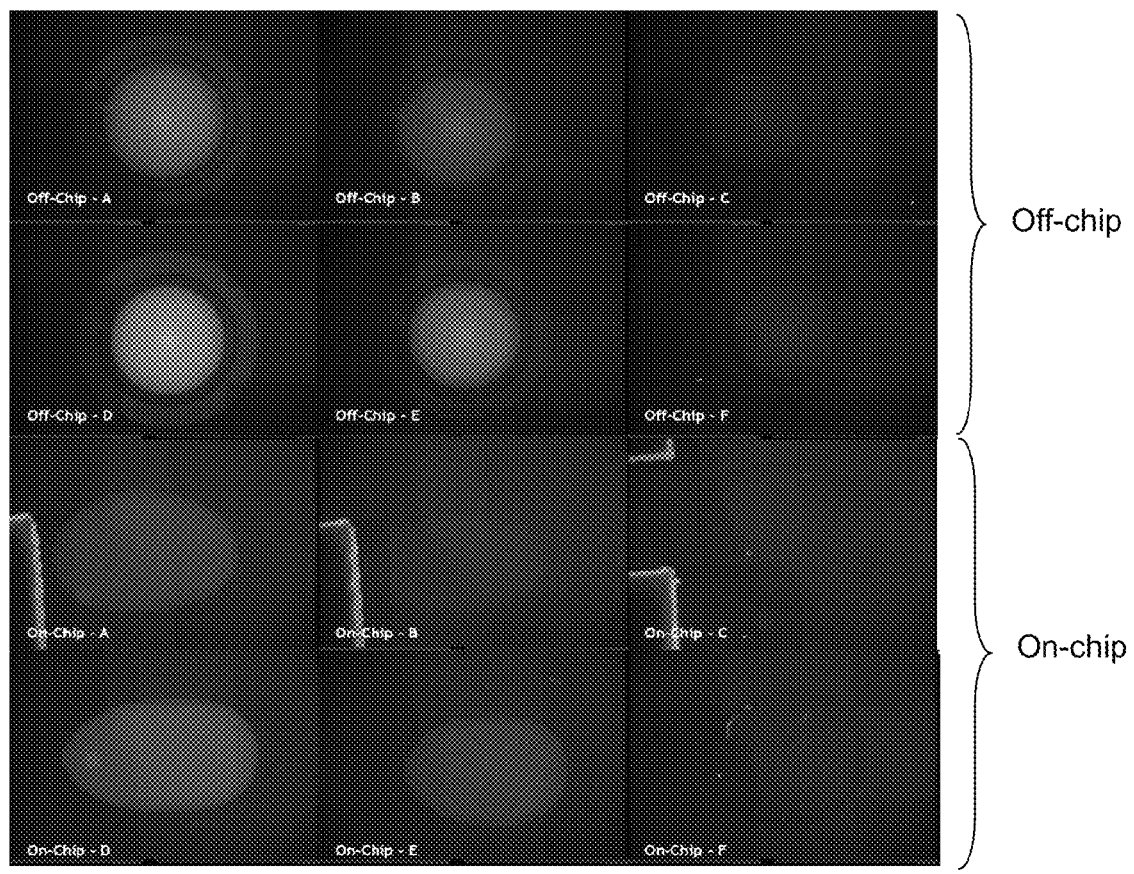
FIG. 5 shows detection of fluorescence in Pompe assays.

FIG. 5 shows detection of fluorescence in Pompe assays. Samples A, B and C were reacted at pH 3.8. Samples D, E and F are reacted at pH 7.0. Samples were removed and analyzed by measuring the fluorescence on a microscope (350 Ex/420 Em). Panels C and F represent samples with substrate, inhibitor but no blood. Panels B and E represent samples with substrate, inhibitor and blood. Panels A and D represent samples with substrate and blood. In the on-actuator sample, the incubation is off-actuator for about 21.5 hours at room temperature and then the sample is mixed 1:1 on-actuator with about 0.4 M bicarbonate buffer, pH 9.0 with the droplet actuator. As shown, the fluorescence increases with time in both the on-actuator and off-actuator samples.

7.7.3 Droplet Actuator Assay of α-Glucosidase Activity

Figure 6A:
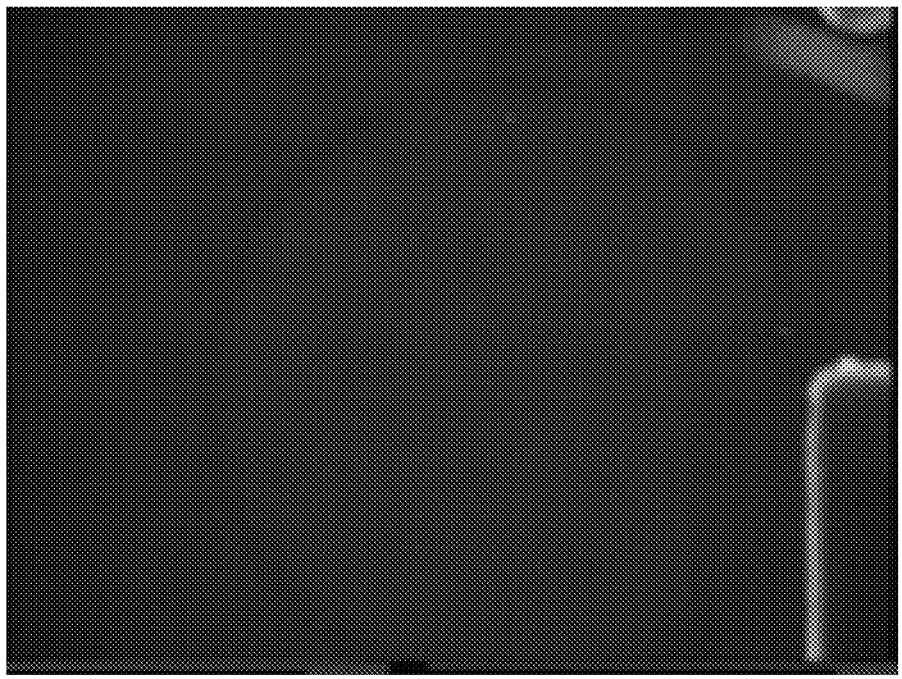
FIGS. 6A and 6B illustrate the physical detection of fluorescence in assays that are conducted substantially entirely in the droplet actuator, i.e., on-actuator.
Figure 6B:
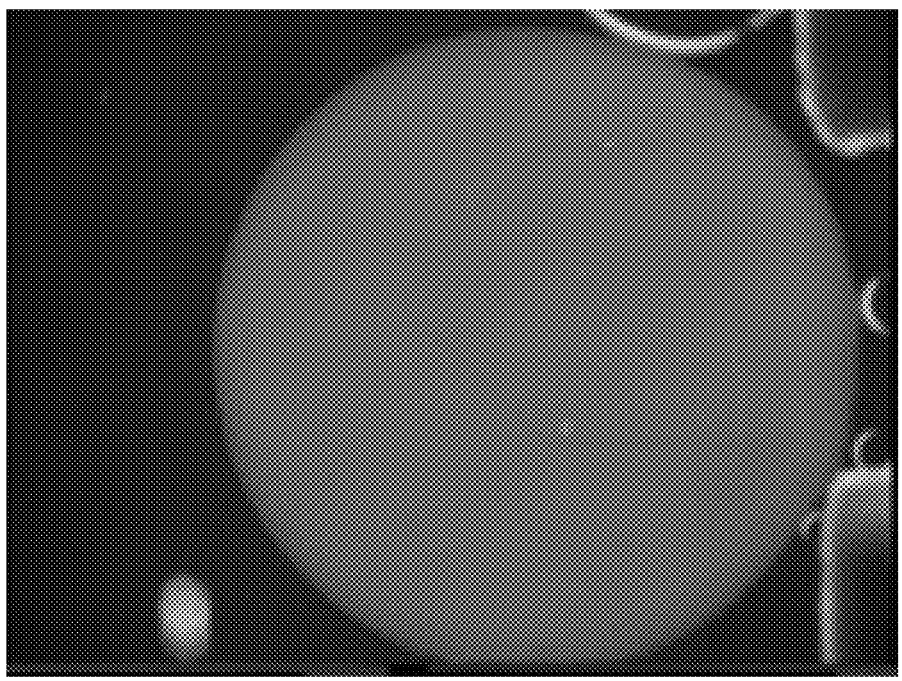

FIGS. 6A and 6B illustrate the physical detection of fluorescence in assays that are conducted substantially entirely in the droplet actuator, i.e., on-actuator. The dried blood spot is reconstituted in about 180 µL of water and added to reaction components giving a final concentration of about 1.4 mM 4-methylumbelliferyl α-D-glucopyranoside in about 0.04M NaAc pH 3.8 or pH 7.0, with or without about 5.9 uM of the inhibitor acarbose. The reaction droplet may be quenched with a droplet comprising NaHCO$_3$, pH 9.0 at a concentration of about 0.1 M for assays that are conducted on the bench, and about 0.4M for assays that are conducted in the droplet actuator. The reactions were incubated at about 25 C for about 22.5 hrs and quenched with NaHCO$_3$. Fluorescence was read on a microscope (350 Ex/420 Em). The unit droplet size used for sample and reagent droplets was about 1 µL.

FIG. 6A shows the fluorescence detected in the presence of water, while FIG. 6B shows the fluorescence detected in the presence of blood. The fluorescence detected in the presence of blood is significantly greater than the minimal amount of fluorescence that is detected in the presence of water.

7.7.4 Comparison of On-Actuator and Off-Actuator Procedures

Table 3 provides a comparison of the results shown in Table 1 vs. the analyses shown in FIGS. 6A and 6B. In particular, Table 3 provides a comparison of the results of an off-actuator bench assay with an on-actuator assay. The ratio of signal in the blood-containing sample to signal in the water control sample are determined for both the procedures conducted off-actuator and on-actuator. The ratio of signals in the off-actuator sample is comparable to the ratio of signals in the on-actuator sample. For diagnosis of Pompe disease, both the off-actuator and on-actuator assays indicate the presence or absence of α-glucosidase activity.

TABLE 3

Off-actuator vs. on-actuator comparison

|  | Off-actuator | On-actuator |
| --- | --- | --- |
| A: Blood + Substrate pH 3.8 | 17813 | 3.39e−7 |
| B: Water + Substrate pH 3.8 | 3214 | 6.84e−8 |
| Signal increase (A/B) | 5.54 | 4.85 |

7.8 Fabry Disease

Figure 7:
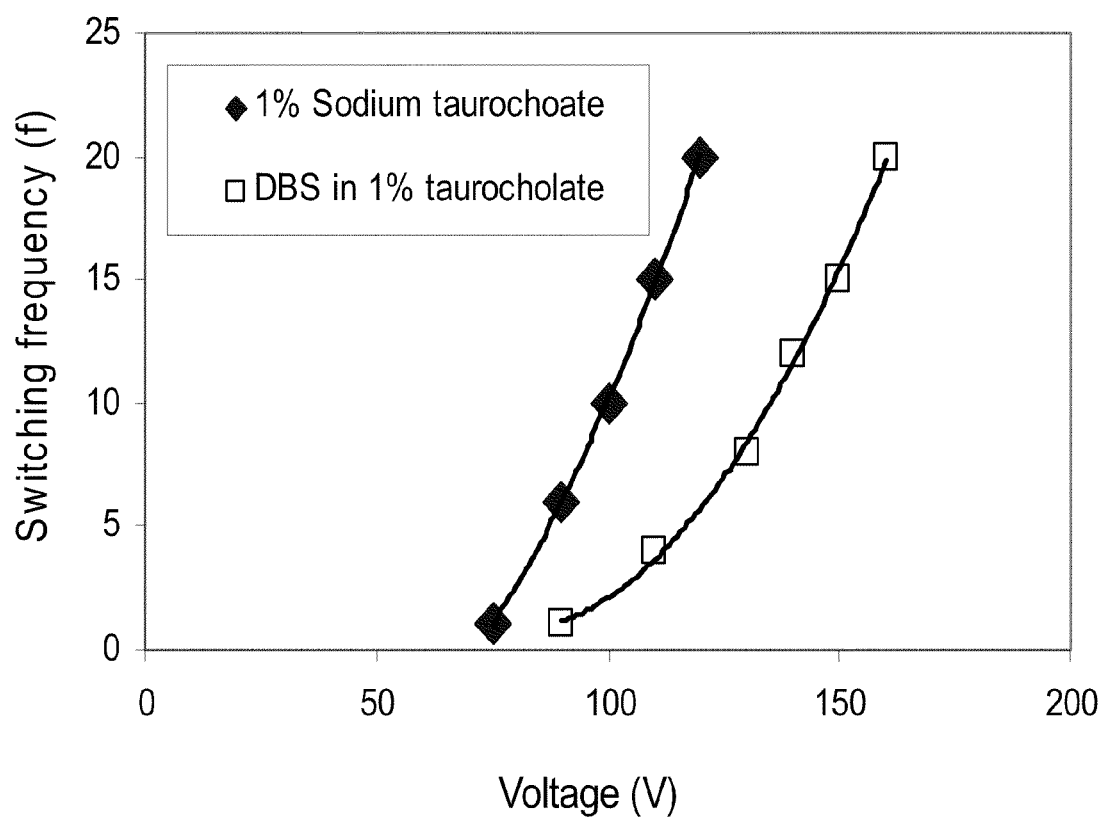
FIG. 7 demonstrates the impact of sodium taurocholate, a component of the α-galactosidase assay, on the switching frequency vs. voltage in the presence and absence of DBS.

FIG. 7 demonstrates the impact of sodium taurocholate, a component of the α-galactosidase assay, on the switching frequency vs. voltage in the presence and absence of DBS. A defect in α-galactosidase is diagnostic of Fabry disease. The plot demonstrates that the reagents for Fabry disease test and the reconstituted blood sample can be manipulated on a droplet actuator by electrowetting. Since droplet transport relies on manipulation of interfacial tension, and since sodium taurocholic acid is a surfactant which can change the interfacial tension, the inventors first evaluated the compatibility of this material with droplet operations on the droplet actuator. A dried blood spot was reconstituted in about 250 µL of 1% (w/v) sodium taurocholic acid. No α-galactosidase reaction is performed. The substrate, 4-methylumbelliferyl α-galactoside was not included and enzymatic activity was not measured. The reaction was incubated for about an hour in a droplet actuator. The droplet actuator utilized a single layer glass actuator, 12 µm parylene C, and 1% Teflon AF. The top substrate was ITO and 1% Teflon AF. The reaction was conducted in the presence and absence of blood. The switching frequency (f) may be determined as a function of the applied voltage (V) for both the sample in the presence of blood, and the sample in the absence in blood. The results indicate that the assay to detect α-galactosidase activity is compatible with the droplet actuator.

7.9 Hunter Syndrome Assay

The invention also provides a novel assay for Hunter syndrome, which is caused by a reduction (or absence) of the enzyme iduronate-2-sulfatase (I2S). One assay according to the invention makes use of 4-methylumbelliferyl-2-sulfate-iduronic acid (acid of 4-methylumbelliferyl-α-iduronate 2-sulphate, 4-MU-I-2SO4) as a substrate. The assay is a two enzyme coupled assay where I2S first cleaves the sulfate from 4-MU-I-2SO4, then L-iduronidase cleaves 4-MU-iduronic acid to release the 4-methylumbelliferyl, generating a fluorescent signal. The assay must be supplemented with L-iduronidase, which is very expensive. The 4-MU-I-2SO4 substrate is also expensive. Generic sulfatase using 4-methylumbelliferyl-sulfate as a substrate will not work because the substrate is susceptible to hydrolysis by numerous other sulfatases in blood.

The invention also provides method which avoids the use of L-iduronidase. In this method, an antibody specific for human iduronate-2-sulfatase is coupled to magnetically responsive beads. The antibody binds the enzyme without inhibiting enzymatic activity. The reconstituted dried blood spot sample is presented to the antibody-bead. The I2S binds to the bead. All unbound material including other sulfatases and hemoglobin are washed away, e.g., using a droplet-based washing protocol. The inexpensive substrate, 4-methylumbelliferyl-sulfate, is presented to the enzyme on the beads and incubated. Sulfate is cleaved off releasing 4-methylumbelliferyl and a fluorescent signal generated. If there is any interference from the beads, then either I2S can be cleaved from the beads and the beads removed before detection or the beads with I2S can be removed after the reaction is complete but just before detection. This assay is much less expensive than the 4-MU-I-2SO4 approach because it does not require the L-iduronidase enzyme or the expensive 4-MU-I-2SO4 substrate. Time to result is also faster because the assay does not require two enzymes to work in series. Removal of hemoglobin from the assay reduces or eliminates signal quench.

The assay may be accomplished on a droplet actuator using droplet operations. For example, an reagent droplet may be supplied on a droplet actuator, the droplet comprising an antibody specific for human iduronate-2-sulfatase coupled to magnetic beads. A sample solution, such as a reconstituted dried blood spot sample or fresh blood sample, may also be provided on the droplet actuator. Sample and reagent sub-droplets may be dispensed from the source droplets and combined using droplet operations to yield an assay droplet. In the assay droplet, the I2S binds to the antibodies on the beads. The beads may be washed, e.g., using a droplet based washing protocol, to remove substantially all unbound material, including other sulfatases and hemoglobin, yielding a washed assay droplet. A droplet comprising 4-methylumbelliferyl-sulfate, may be combined with the washed assay droplet to yield a detection droplet. The detection droplet may be incubated. During incubation, sulfate is cleaved off releasing 4-methylumbelliferyl and a fluorescent signal is generated in the detection droplet. The fluorescent signal may be detected, and Hunter disease may be diagnosed based on the signal.

7.10 Multiplexed Assays On-Platform by Kinetic Method

Stock solutions of 4-methylumbelliferylglycoside substrates were prepared in DMSO at concentrations of 70-100 mM. The 4-MU glycosides were then diluted into working assay buffers specific for each glycosidase: Pompe disease (α-D-glucosidase), 10 mM 4-MU-α-D-glucoside, 6 µM acarbose, 0.1 M sodium acetate, pH 3.8; Hurler disease (α-L-iduronidase), 10 mM 4-MU-α-L-iduronide, 5 µg/ml D-saccharic 1,4-lactone monohydrate, 0.04 M sodium citrate, pH 2.8; Fabry disease (α-D-galactosidase), 10 mM 4-MU-α-D-galactoside, 75 mM N-Acetylgalactosamine, 0.1 M sodium citrate, pH 4.6, 1% sodium taurocholate; and β-D-glucuronidase (control), 10 mM 4-MU-β-D-glucuronide, 0.1 M sodium acetate, pH 4.8. Upon completion of each assay, the enzymatic reactions were terminated with 0.1 M sodium bicarbonate, pH 10 and read for fluorescence. Punches from dried blood spots (DBS), 3 mm in diameter, were reconstituted in 150 µl water or 150 µl water with 0.1% Tween 20.

The on-droplet actuator LSD enzyme assay format was as follows. All droplet volumes were 300 nL. Reconstitute 3 mm diameter punch from one DBS in 150 µL 0.1% Tween 20. Dispense 1 droplet DBS extract and 1 droplet assay mix and merge. Split DBS extract/assay mix into two droplets. Immediately merge 1 droplet DBS extract/assay mix with 1 droplet termination buffer. Read fluorescence (Ex/Em, 350/420 nm) for zero time value. Incubate remaining 1 droplet DBS extract/assay mix for 4 hours. Merge 1 droplet DBS extract/assay mix with 1 droplet termination buffer. Read fluorescence (Ex/Em, 350/420 nm) for 4 hour time value.

Figure 8:
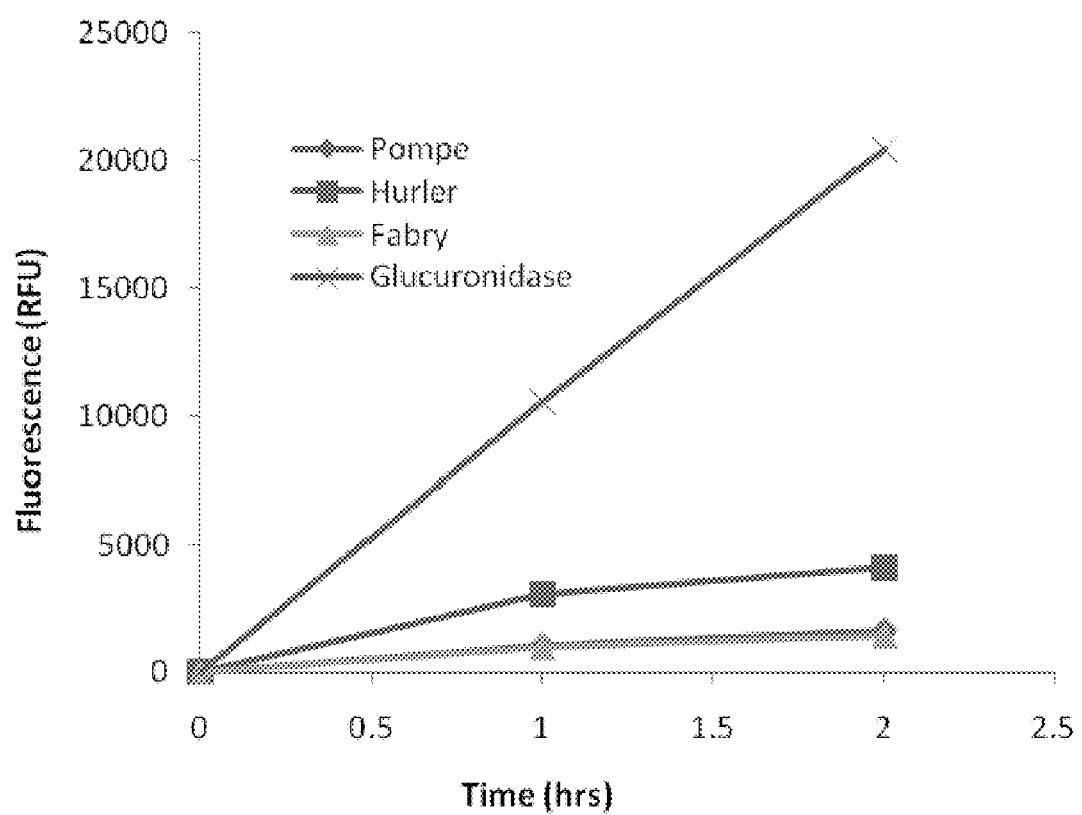
FIG. 8 shows the enzymatic activity time-course for four assays performed on the bench.

FIG. 8 shows the enzymatic activity time-course for four enzyme assays performed on the bench. Each time point, 0, 60 or 120 minutes, is an end point assay meaning the reaction is terminated by mixing with an alkaline pH termination buffer. The termination buffer also has an additional benefit of increasing the fluorescent signal of the product. The enzyme activity increased with time with sufficient signal being generated in two hours to measure the activity for all four enzymes in the DBS. The percent increase in activity over background for each enzyme in a two hour bench assay ranged from 36-301%.

Figure 9:
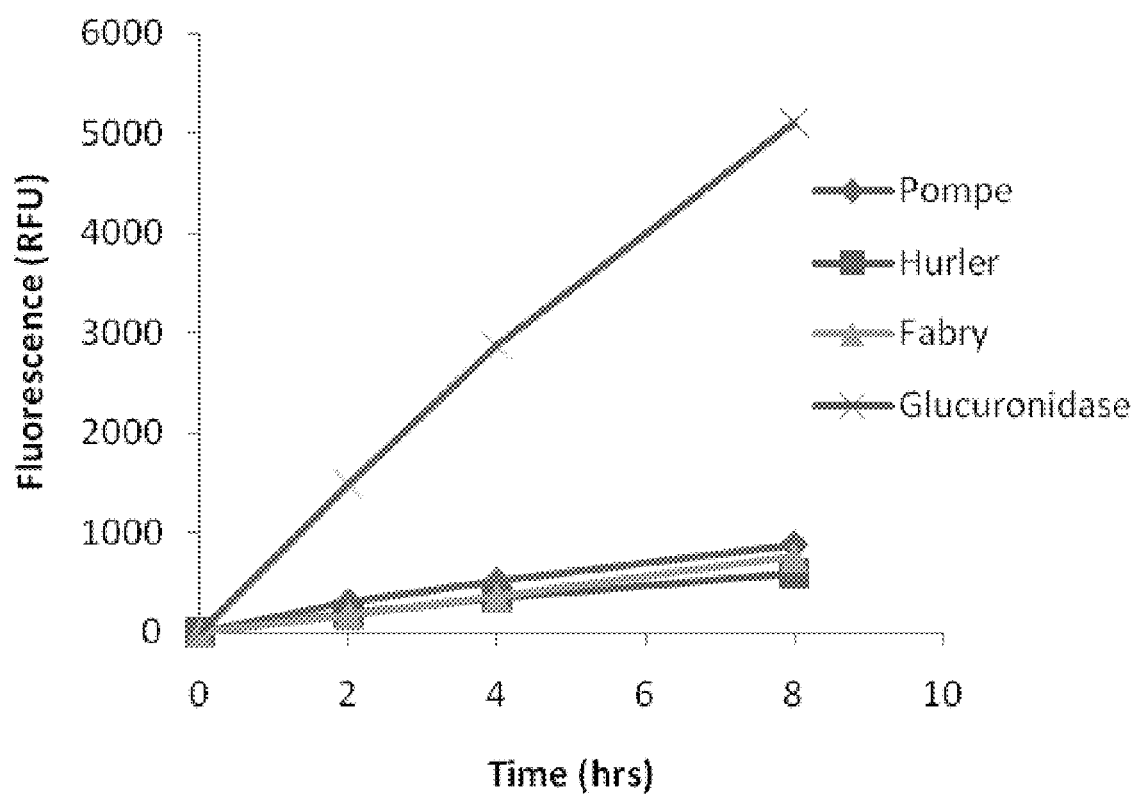
FIG. 9 shows the time-course of enzyme activity for 4 enzymes on a droplet actuator.

FIG. 9 shows the time-course of enzyme activity for 4 enzymes on a droplet actuator. The on-droplet actuator protocol was as follows: Droplets of DBS are dispensed and mixed with droplets of the respective 4-MU substrates on the droplet actuator. Each reaction mixture is incubated for 0, 2 hrs, 4 hrs, and 8 hrs and terminated at the end of incubation by a stop buffer droplet and the fluorescence is measured by marching the droplets through the field of view of the fluorimeter. For 2 hr incubation on the droplet actuator, the percent increase in activity over background for each enzyme ranged from 38-261% which matched closely with the bench data even though the volume of reactions on-droplet actuator were performed on 300 nL droplets compared to 25 µL volumes on the bench. Even though at 8 hr incubation there is a 125-895% increase in fluorescence on-droplet actuator, in interest of keeping the incubation time shorter and providing rapid results the reactions were incubated for 4 hrs with the increase in activity ranging from 71-503%. These experiments were performed at room temperature.

The 4 enzymatic assays (Pompe, Fabry, Hurler, β-Glucuronidase) were performed on a single droplet actuator. The droplet actuator was loaded with DBS samples, substrates, and stop buffer and the software was preprogrammed to run the specific protocols for dispensing, transport, and mixing the sample and substrate, incubation for 4 hrs, and then dispensing and mixing the reaction mixtures with the stop buffer and finally marching the droplets to the fluorimeter and disposing to waste reservoir. The user is only involved in loading the droplet actuator and after that, it is walk away automation.

Figure 10:
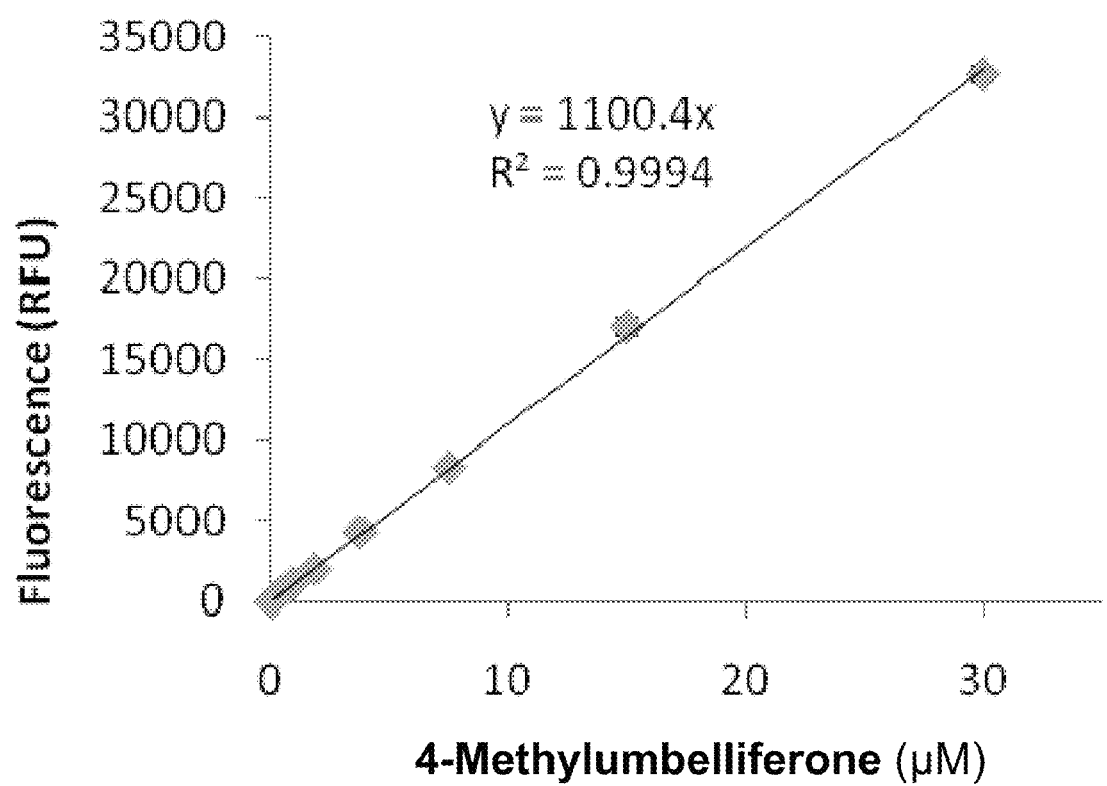
FIG. 10 shows curves showing the limit of detection (measured as mean of 10 zero values+3 standard deviations above the mean) of 4-methylumbelliferone on a droplet actuator.

The sensitivity of the droplet actuator platform for detecting 4-methylumbelliferyl, which is the product of the glycosidase assays used for LSD detection, was measured on two different droplet actuators. A standard curve of 4-methylumbelliferone ranging in concentration from 0.23-30 µM was prepared in termination buffer. A 300 nL droplet of each concentration was dispensed onto a droplet actuator, transported to the fluorimeter, and the fluorescence measured. The fluorescence signal from a droplet of termination buffer without 4-methylumbelliferone was subtracted from each of the standard values. The average values for the duplicate standard curves from both the droplet actuators are shown in FIG. 10 along with standard deviation even though the error bars can only be faintly discerned because the standard deviation of all the measurements between droplet actuators was extremely small. The limit of detection (measured as mean of 10 zero values+3 standard deviations above the mean) of 4-methylumbelliferone for the current configuration of our analyzer in 300 nL droplets is 14 nM.

Figure 11:
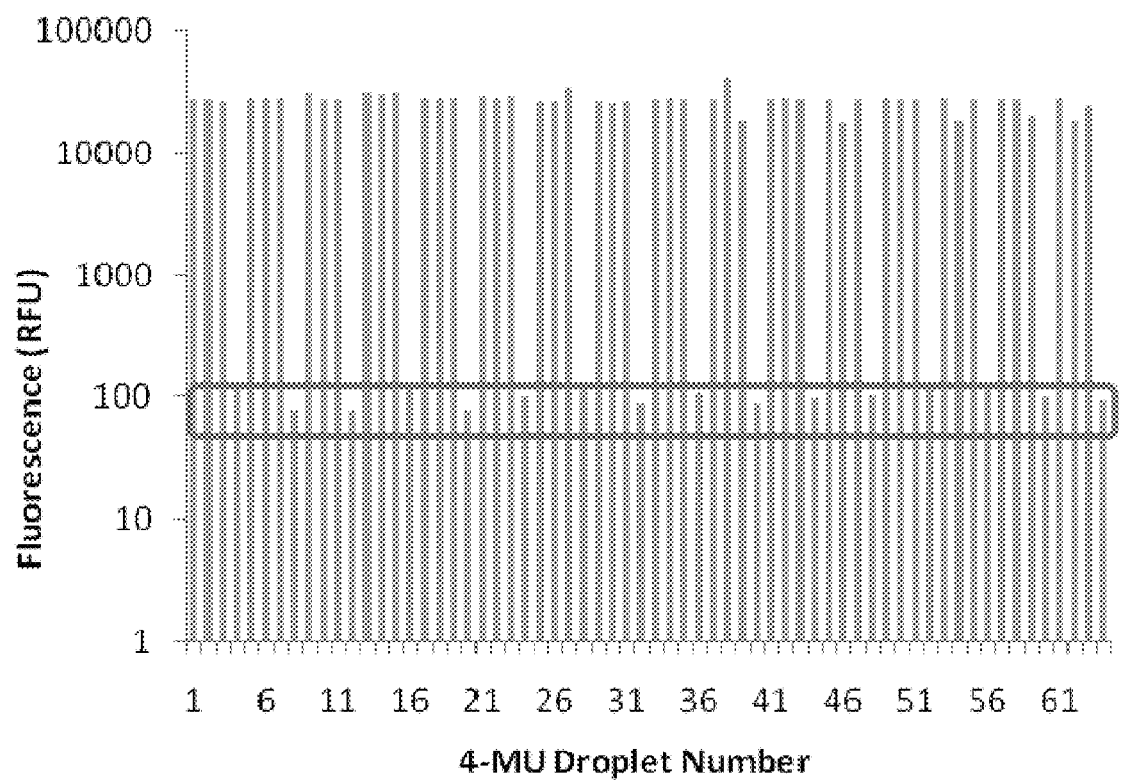
FIG. 11 shows results of a droplet cross-contamination study.

One potential concern of the assay on-droplet actuator is cross contamination from one sample to another since many droplet pathways can cross each other. Droplet pathway cross over is generally minimized. For the results shown in FIG. 11, 3 droplets of 30 µM 4-MU were run across the fluorescence detection spot followed by a droplet with 0 µM 4-MU and this cycle was repeated 16 times in 2 cSt Silicone oil with Triton X15. The y-axis is on log scale in order to show the zero values more clearly. The fluorescence from the zero droplet does not increase after 16 runs as shown in the highlighted band. A total of 64 droplets (48 high 4-MU droplets and 16 zero droplets) were run across the detector.

Figure 12:
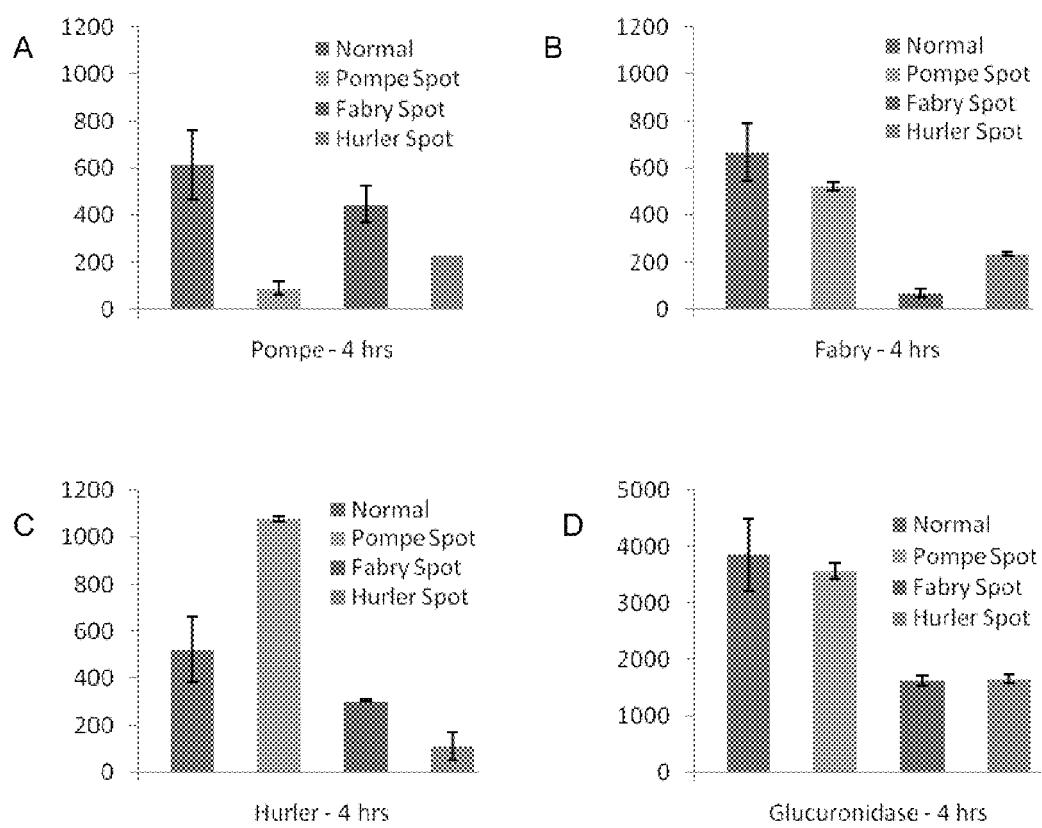
FIG. 12 shows the discrimination of a diseased dried blood spot from a normal dried blood spot.

Normal and diseased DBS extract were run on-droplet actuator for 4 hours. FIG. 12 shows the discrimination of a diseased DBS from a normal DBS. In FIG. 12A, the first vertical bar shows fluorescence from 8 normal spots assayed with Pompe substrate, the next vertical bar shows a Pompe diseased spot run with Pompe substrate, and the next two bars show a Fabry diseased spot and Hurler diseased spot respectively run with Pompe substrate. It can be seen that the Pompe diseased spot shows reduced activity compared to the normal spots and also compared to the Fabry diseased spot and Hurler diseased spot, demonstrating the there is no cross reactivity between Pompe diseased spot and other substrates. The second vertical bar in FIG. 12D shows fluorescence from glucuronidase assay run with the Pompe diseased spot, which shows normal level of activity. Glucuronidase is run as a control. Similarly in FIG. 12B, 8 normal spots, Pompe spot, Fabry spot, and Hurler spot are run with Fabry substrate. It shows reduced activity only for the Fabry spot and normal level of activity for other spots. In FIG. 12C, 8 normal spots, Pompe spot, Fabry spot, and Hurler spot are run with Hurler substrate. It shows reduced activity only for the Hurler spot and higher level of activity for other spots. FIG. 12D shows about the same level of activity for all the spots where each diseased spot and 8 normal spots are run with substrate for glucuronidase. All the assays were performed for 4 hrs on-droplet actuator at room temperature. The activity in diseased spots is below the average of normal spots by at least 2 standard deviations. All the enzymatic assays will have increased activity at 37° C. and therefore normal spots would give increased fluorescence and better separation from diseased spots. Thermal stabilization has recently been added by the inventors to an instrument with measured standard deviation of 0.17° C. at 37° C.

Figure 13:
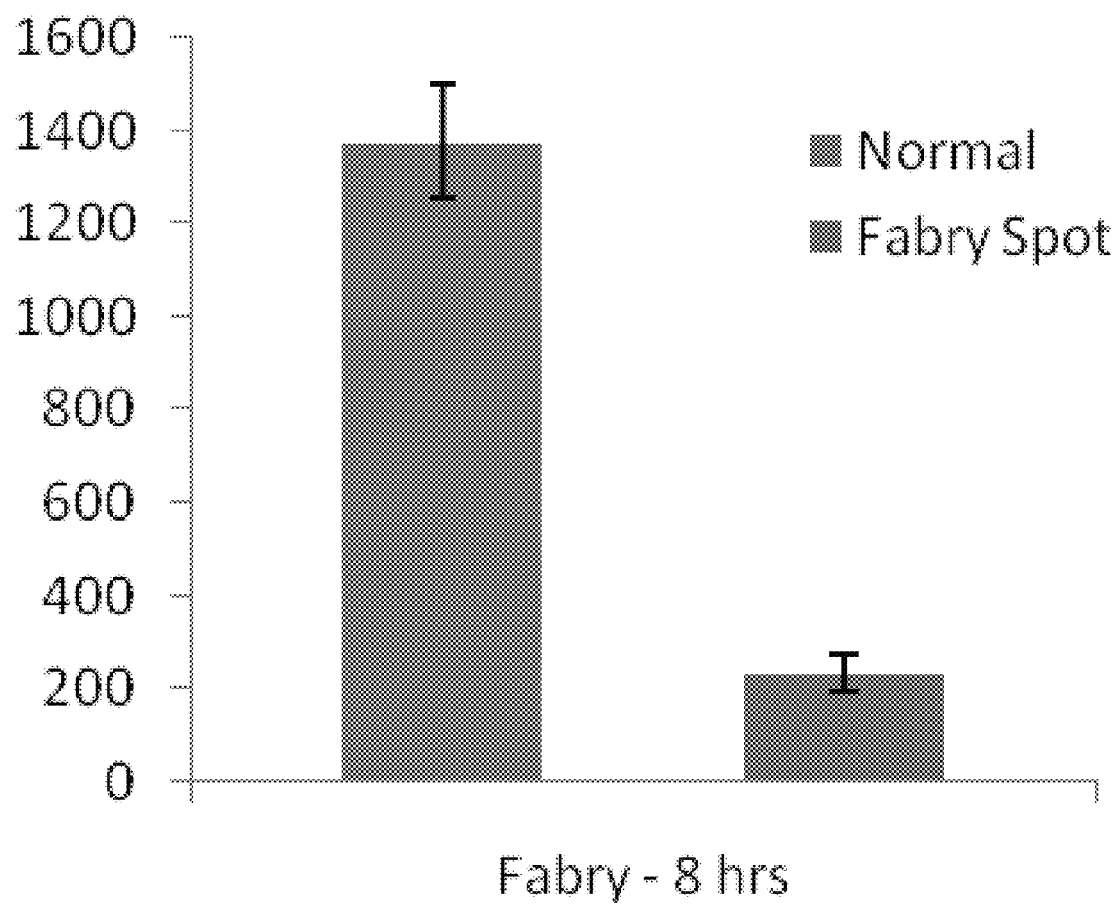
FIG. 13 shows the fluorescence obtained from a Fabry diseased spot along with the average obtained from 8 normal spots reacted with Fabry substrate.

In order to increase the separation between the measured activity of normal spots and diseased spots, the following parameters were explored:

Reaction Incubation Time: FIG. 13 shows the fluorescence obtained from a Fabry diseased spot (same spot as shown in FIG. 12) along with the average obtained from 8 normal spots reacted with Fabry substrate over an incubation time of 8 hrs. The fluorescence from a normal spot incubated for 8 hrs is separated by 9 standard deviations from that of the Fabry diseased spot as compared to a separation of 5 standard deviations for a 4 hr reaction incubation time.

Figure 14:
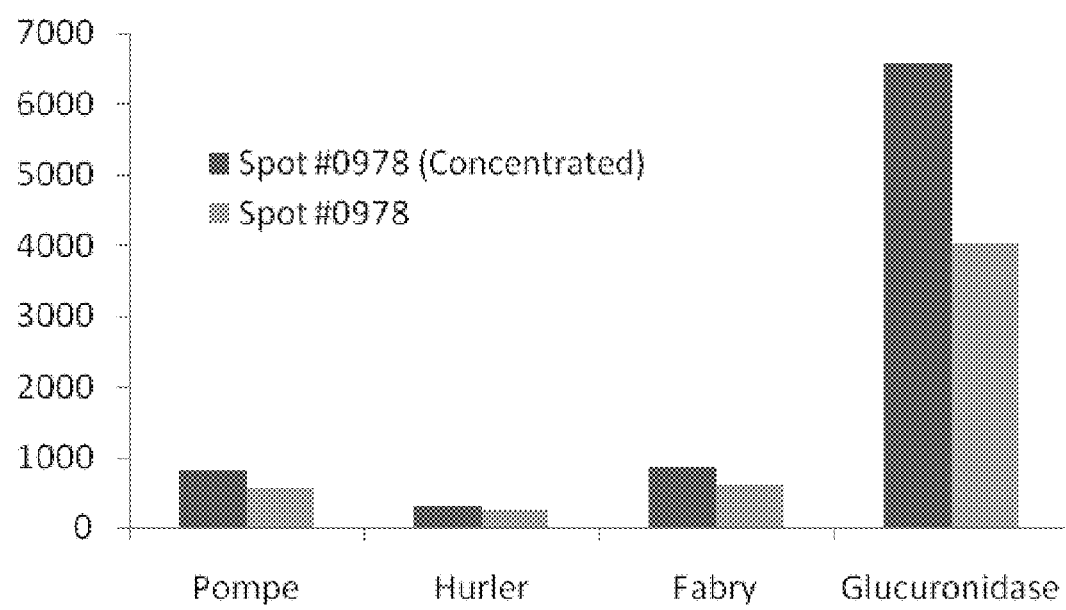
FIG. 14 shows results of a study to increase signal where 4 enzymatic assays were performed on a single normal spot.

Reconstitution Volume In another experiment to obtain increased signal, the reconstitution volume was reduced from 150 µL (used for results in FIG. 12) to 90 µL. This would essentially lead to concentration of the enzymes in the DBS extract. The effect can be seen in FIG. 14 where 4 enzymatic assays were performed on a single normal spot. The signal from the 90 µL extract, denoted as 'concentrated', is higher than the signals from a 150 µL extract by an average factor of 1.5 (except for Hurler where it was only 1.1). This generally corresponds to the concentration factor of 150 µL/90 µL=1.66. The droplet volume on-droplet actuator remained same at 300 nanoliters.

Figure 15:
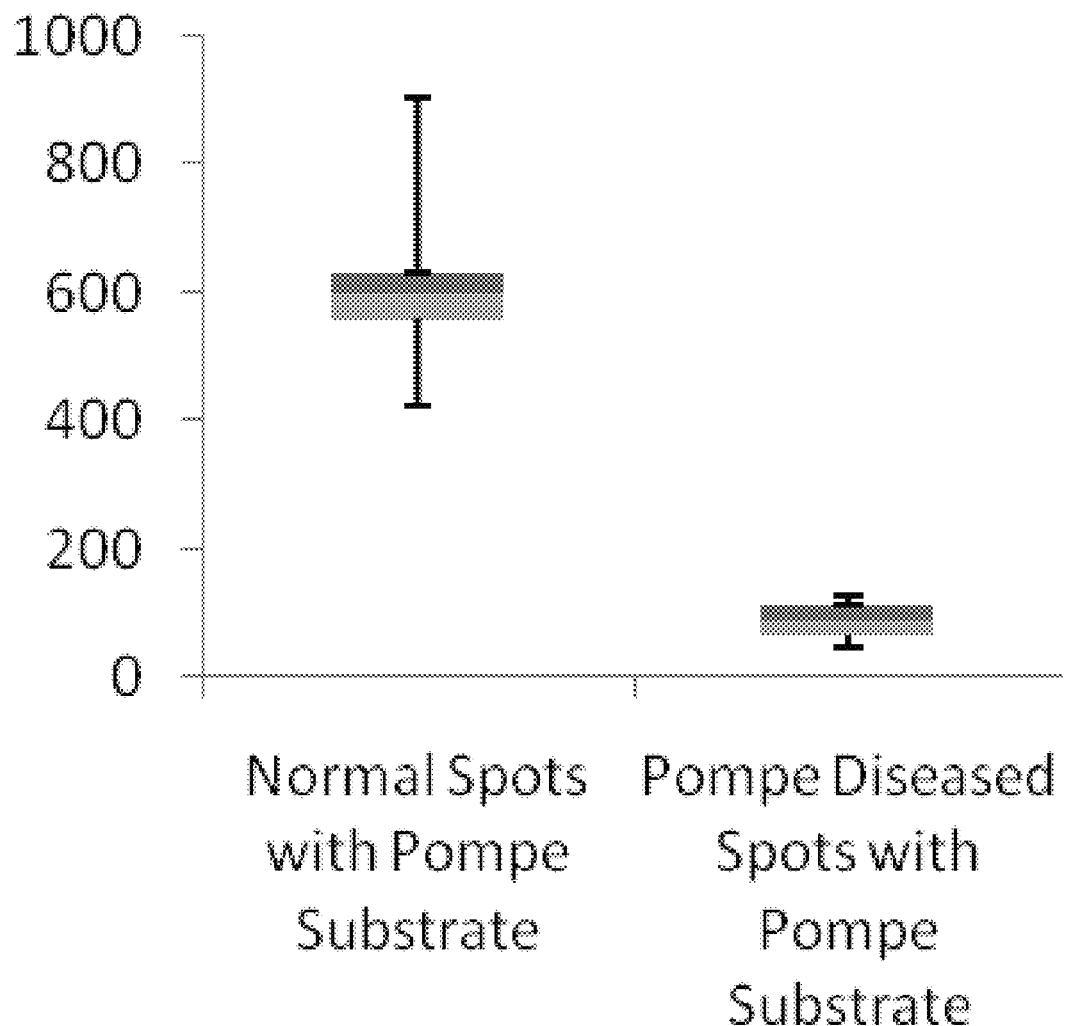
FIG. 15 shows a box plot comparing fluorescence obtained from 8 normal spots compared with that from 4 Pompe disease spots.

Pompe Diseased Spots: FIG. 15 shows a box plot comparing fluorescence obtained from 8 normal spots compared with that from 4 Pompe disease spots. The bars represent the minimum and maximum signals obtained while the boxes represent the fluorescence levels at 75th percentile, median, and the 25th percentile. Even with 4 hr incubation and none of the improvements suggested above, it can be noted that the diseased spots are clearly separated from the normal spots.

Discrimination of normal spots from diseased spots in population based screening may be further enhanced by controlling droplet actuator temperature, using more concentrated DBS extracts, increasing the incubation time, and/or better assessment of background.

7.11 Enzyme Cascade Detection

The invention also provides a new enzyme cascade detection method to generate signal for ELISA and other assays on-actuator. In the current ELISA format, an enzyme, such as ALP or HRP, is conjugated to a reporter antibody or streptavidin. A substrate is delivered to the complex and a long-lived, chemiluminescent product is enzymatically produced. The novel approach of the invention makes use of an enzyme or a series of enzymes to generate a signal amplification cascade. The cascade improves the sensitivity of the detection system. As an example, the signal cascade may terminate with firefly luciferase converting luciferin to light in a "flash" chemiluminescence reaction.

In one example, β-galactosidase may be coupled to an antibody or streptavidin. Luciferin-β-galactoside, which is not a substrate for luciferase, may be delivered to the immuno-complex, incubated and hydrolyzed to free luciferin and galactose by the β-galactosidase. The luciferin is then delivered to the PMT where it is mixed with excess ATP and firefly luciferase. All of the luciferin is rapidly converted to light in a flash reaction. Beta-galactosidase can form 700 pmole luciferin per ng enzyme per minute which is equivalent to $7^{12}$ photons per second. In this method the background is very low, and unlike the currently used glow substrates, all of the assay signal may be captured in the short time of the flash reaction. This method also reduces or eliminates the currently observed contamination of long-lived glow chemiluminescent products on-actuator because of the short life time of the luciferin product. It just decays away spontaneously so washing to remove glowing products is eliminated. This system is not a signal regeneration loop like the one used in pyrosequencing.

The steps in the flash assay may be achieved using droplet operations. For example, a droplet protocol may include providing a first droplet comprising β-galactosidase-antibody or β-galactosidase-streptavidin. A second droplet including luciferin-β-galactoside, which is not a substrate for luciferase, may be combined with the first droplet to yield a third droplet. The third droplet may be incubated and hydrolyzed to free luciferin and galactose by the beta-galactosidase. The third droplet including freed luciferin may be transported using droplet operations into the presence of a sensor, such as a PMT, where it is combined using droplet operations with a droplet comprising excess ATP and luciferase (e.g., firefly luciferase). The luciferin is rapidly converted to light in a flash reaction.

The flash assay of the invention may be performed on a droplet actuator, in oil. In some embodiments, a common detection window is used for multiple assays. Where glow assays are used, microdroplets from previous reactions may create background signal that interferes with detection of subsequent droplets. The flash assay of the invention provides a means whereby multiple droplets may be processed for detection in a common detection window on a droplet actuator in a filler fluid with little or no background signal remaining between droplets. For example, little or no background signal from a previous droplet may remain in oil or in microdroplets in oil in proximity to the detection window. In some cases, background signal interference from previous droplets is substantially eliminated by using the flash procedure.

In flash assays, it may be useful to use wash droplets that include the trigger solution to clean droplet transport lanes. Electrode paths that have been used to transport the substrate may be washed by transporting one or more wash droplets across some portion or all of the same area. The wash droplets may include the flash enzyme. For example, the wash droplet (s) may include luciferase or luciferase and ATP.

As another example, acridinium ester (AE) may be used as a chemiluminescent label in a flash assay of the invention. The AE signal quickly rises to a high value, typically in less than about 10, 9, 8, 7, 6, 5, 4, 3, 2 or 1 seconds upon addition of the trigger solution. The signal decays to very low values, typically in less than about 60, 30, 20, or 10 seconds. This may eliminate contamination on the detection loop and the detection spot. However, there contamination may still be present on the wash lanes and the incubation region by free secondary antibody bound with AE which can potentially affect the subsequent assays performed on the same lane. Transporting 1, 2, 3, 4, 5, 6, 7, 8, 9, 10, or more droplets of the AE trigger solution over the electrodes that are contaminated with antibody bound with AE would produce chemiluminescence which would decay quickly, substantially eliminating AE contamination.

7.12 Temperature Control

The droplet actuator of the invention may include a means for controlling the temperature of the droplet actuator or a region of the droplet actuator. Among other things, thermal control is useful for various protocols requiring control of droplet temperature during incubation.

In general, thermal control may be provided in three ways: (1) thermal control of the entire droplet actuator; (2) thermal control of a region of a droplet actuator using a heater that is in contact with or in proximity (such as an infrared lamp) to the controlled region; and (3) thermal control of a region of the droplet actuator using a heater that is integrated into the droplet actuator (e.g., in the substrate comprising the path or array of electrodes and/or in a top substrate of the droplet actuator, when present). Combinations of the foregoing approaches are also possible.

In an integrated heater approach, temperature zones can be created and controlled using thermal control systems directly integrated into the droplet actuator. Thermal control is enhanced by locating the heating elements proximate to the droplets and reducing the parasitic thermal losses between the heater and the droplet. Heating elements can be integrated into the top substrate and/or bottom substrate of the droplet actuator, located within the droplet operations gap. Various hybrids of the foregoing approaches are also possible, e.g., partially in a substrate and partially in the gap.

Integrating heating elements onto the droplet actuator also enables the use of multiple distinct thermal zones within the droplet actuator. Droplets can be transported into a thermal zone having a temperature suitable for a particular enzyme reaction. In a multiplexing application, a droplet actuator may be provided with different thermal zones, and each enzyme reaction may be incubated in a thermal zone appropriate for the particular enzyme being tested. Similarly, quenching thermal zones may also be provided having temperatures established to slow or stop a reaction, such as an enzyme reaction, in a droplet. A droplet may be transported into a thermal zone having a quenching temperature (low or high) in order to slow or stop the reaction. Droplets can be physically transported using droplet operations temperature zones of different fixed temperatures to perform the various steps of the enzyme reaction. The droplet actuator layout is scalable, such that a droplet actuator may include a few as one heating zone up to tens, hundreds or more heating zones. In an alternative embodiment, temperature is controlled by flowing or recirculating heated filler fluid through the droplet actuator and around the droplets.

Heaters may, in some embodiments, be formed using thin conductive films. Examples of suitable thin films include Pt heater wires and transparent indium-tin-oxide (ITO). ITO provides better visualization of the droplets for real-time observation. A remotely placed conventional thermocouple (TC) for temperature regulation can also be used. In one embodiment, tiny metal (e.g., copper) vias in a PCB substrate are used to create tight thermal junctions between the liquid and the remote TC. Further, sample temperature can be determined by monitoring the copper via using a surface mount thermistor or an infrared sensor. One advantage of using a thermistor for temperature measurement is that they are small enough (2×2 mm) to be soldered directly on the droplet actuator, while an advantage of using IR for heating is that it is a non-contact method which would simplify the interfacing. Because the thermal conductivity of copper is at least 700 times greater than the FR-4 substrate (350-390 W/m·K versus 0.3-0.5 W/m·K) the temperature of a Cu via will accurately represent the temperature inside the liquid. Heaters may be integrated on the bottom and/or top (when present) substrate of the droplet actuator and on the bottom and/or top surface of either substrate, or integrated within the structure of either substrate.

Heaters may be used to create a continuous temperature gradient across the droplet actuator or across a region of a droplet actuator (e.g., from 100 to 50° C.). The use of a continuous gradient will eliminate the need to overcome the steep temperature gradients found along the edge of the heater blocks. A controlled temperature gradient may enhance the functionality of the device by allowing protocols with arbitrary numbers of temperature points to be implemented. Each enzyme reaction droplet may be transported into a region of the temperature gradient most suitable for conducting the particular enzyme reaction. The droplets will be transported to and held at the appropriate location in the thermal gradient to achieve a target temperature.

7.13 Systems

As will be appreciated by one of skill in the art, the invention may be embodied as a method, system, or computer program product. Accordingly, various aspects of the invention may take the form of hardware embodiments, software embodiments (including firmware, resident software, microcode, etc.), or embodiments combining software and hardware aspects that may all generally be referred to herein as a "circuit," "module" or "system." Furthermore, the methods of the invention may take the form of a computer program product on a computer-usable storage medium having computer-usable program code embodied in the medium.

Any suitable computer useable medium may be utilized for software aspects of the invention. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include some or all of the following: an electrical connection having one or more wires, a portable computer diskette, a hard disc, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Computer program code for carrying out operations of the invention may be written in an object oriented programming language such as Java, Python, Smalltalk, C++ or the like. However, the computer program code for carrying out operations of the invention may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

Certain aspects of invention are described with reference to various methods and method steps. It will be understood that each method step can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the methods.

The computer program instructions may also be stored in a computer-readable memory that can direct a computer or other programmable data processing apparatus to function in a particular manner, such that the instructions stored in the computer-readable memory produce an article of manufacture including instruction means which implement various aspects of the method steps.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing various functions/acts specified in the methods of the invention.

8 CONCLUDING REMARKS

The foregoing detailed description of embodiments refers to the accompanying drawings, which illustrate specific embodiments of the invention. Other embodiments having different structures and operations do not depart from the scope of the present invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions and examples are intended as a part of the description of the invention. It will be understood that various details of the present invention may be changed without departing from the scope of the present invention.

We claim:

1. A method of conducting a droplet based enzyme assay comprising:
   (a) providing an immiscible fluid comprising:
      (i) a sample droplet comprising an enzyme; and
      (ii) one or more reagent droplets comprising:
         (1) a substrate which is modified in the presence of the enzyme yielding one or more signal-producing products; and
         (2) optionally, other reagents sufficient to produce activity of the enzyme;
   (b) combining the sample droplet and the one or more reagent droplets in the immiscible fluid to yield a reaction droplet effecting an enzyme reaction in the immiscible fluid; and
   (c) measuring signal produced by the one or more signal producing products
   (d) correlating the signal to the enzyme activity.

2. The method of claim 1 wherein steps 1(b) and 1(c) are accomplished without removing the sample droplet, one or more reagent droplets, or reaction droplet from the immiscible fluid.

3. The method of claim 1 wherein step 1(a) further comprises activating one or more electrodes to mediate dispensing of the sample droplet.

4. The method of claim 1 wherein step 1(a)(ii) further comprises activating one or more electrodes to mediate dispensing of the one or more reagent droplets.

5. The method of claim 1 wherein step 1(b) further comprises activating one or more electrodes for combining the sample droplets and the one or more reagent droplets.

6. The method of claim 1 further comprising dividing the reaction droplet into two or more sub-droplets.

7. The method of claim 6 wherein dividing the reaction droplet further comprises activating one or more electrodes to divide the reaction droplet into two or more sub-droplets.

8. The method of claim 7 further comprising:
   (a) immediately following the dividing step, combining one of the sub-droplets with a quenching droplet to yield a time 0 droplet; and
   (b) detecting signal from the time 0 droplet.

9. The method of claim 8 further comprising:
   (a) incubating one of the sub-droplets for a predetermined period of time;
   (b) combining the incubating droplet with a quenching droplet to yield an endpoint droplet; and
   (c) detecting signal from the endpoint droplet.

10. The method of claim 9 further comprising assessing modification of the substrate by the enzyme based on differences in signal in the time 0 droplet and the endpoint droplet.

11. The method of claim 1 further comprising:
    (a) providing multiple sample droplets comprising an enzyme;
    (b) incubating two or more of the sample droplets for different periods of time;
    (c) measuring endpoint signals for each of the two or more of the sample droplets;
    (d) constructing a curve using the endpoint signals; and
    (e) calculating enzyme activity based on the curve.

12. The method of claim 1 wherein the sample droplet has a volume which is less than about 1000 nL.

13. The method of claim 1 wherein the sample droplet has a volume which is less than about 500 nL.

14. The method of claim 1 wherein the sample droplet has a volume which is less than about 250 nL.

15. The method of claim 1 wherein the sample droplet has a volume which is less than about 100 nL.

16. The method of claim 1 wherein the one or more reagent droplets each has a volume which is less than about 1000 nL.

17. The method of claim 1 wherein the one or more reagent droplets each has a volume which is less than about 500 nL.

18. The method of claim 1 wherein the one or more reagent droplets each has a volume which is less than about 250 nL.

19. The method of claim 1 wherein the one or more reagent droplets each has a volume which is less than about 100 nL.

20. The method of claim 1 wherein the reaction droplet has a volume which is less than about 2500 nL.

21. The method of claim 1 wherein the reaction droplet has a volume which is less than about 1000 nL.

22. The method of claim 1 wherein the reaction droplet has a volume which is less than , about 750 nL.

23. The method of claim 1 wherein the reaction droplet has a volume which is less than about 500 nL.

24. The method of claim 1 wherein the enzyme exhibits abnormal enzyme activity.

25. The method of claim 1 wherein the substrate comprises a glycoside substrate.

26. The method of claim 1 wherein the substrate releases a fluorophore upon contact with the enzyme.

27. The method of claim 26 wherein two or more instances of the method are conducted simultaneously using different fluorophores for each enzyme tested.

28. The method of claim 26 wherein the fluorophore comprises 4-methylumbelliferyl.

29. The method of claim 1 wherein the substrate comprises a glycoside substrate which releases a fluorophore upon contact with the enzyme.

30. The method of claim 1 wherein the substrate comprises a glycoside substrate comprising glucose, galactose, fucose, mannose, sialic acid, hexose, hexosamine and/or N-acetylated hexosamine.

31. The method of claim 30 wherein the substrate comprises a 4-methylumbelliferyl glycoside.

32. The method of claim 1 further comprising reducing or eliminating reaction contaminants associated with the substrate prior to yielding the reaction droplet.

33. The method of claim 32 wherein the reducing or eliminating reaction contaminants comprises photobleaching the substrate prior to yielding the reaction droplet.

34. The method of claim 1 wherein the substrate comprises a 4-methylumbelliferyl glycoside substrate.

35. The method of claim 34 further comprising photobleaching the substrate prior to yielding the reaction droplet.

36. The method of claim 1 wherein the immiscible fluid is a liquid and the liquid comprises a filler fluid.

37. The method of claim 1 wherein the immiscible fluid comprises a silicone oil.

38. The method of claim 36 wherein the filler fluid comprises a surfactant.

39. The method of claim 38 wherein the surfactant comprises nonionic low hydrophile-lipophilp balanced (HLB) surfactant.

40. The method of claim 39 wherein the HLB is less than about 10.

41. The method of claim 39 wherein the HLB is less than about 5.

42. The method of claim 39 wherein the surfactant is selected from the group consisting of octylphenol ethoxylate; sorbitane trioleate; sorbitan tristearate; sorbitane monooleate; sorbitane monostearate;

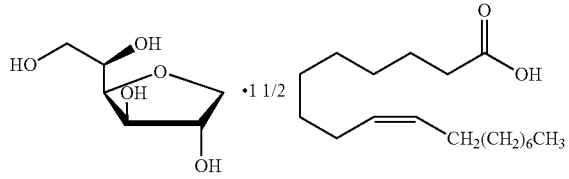

and fluorinated surfactants.

43. The method of claim 1 wherein:
 (a) the sample droplet comprises a reconstituted blood sample;
 (b) the blood sample is reconstituted in a single universal reconstitution solution;
 (c) the blood sample is divided to yield two or more reaction droplets; and
 (d) two or more of the reaction droplets are each combined with one or more sets of one or more reagent droplets, each such set comprising reagents selected for establishing reaction conditions for a different enzyme.

44. The method of claim 43 wherein the universal reconstitution solution comprises a saline solution.

45. The method of claim 43 wherein the universal reconstitution solution comprises water.

46. The method of claim 1 further comprising combining each of two or more sample droplets with reagent droplets selected for establishing reaction conditions for a different enzyme.

47. The method of claim 46 wherein the sample droplets comprise fresh blood and/or reconstituted blood spot.

48. The method of claim 46 wherein the sample droplets comprise a dried blood spot reconstituted in water.

49. The method of claim 46 wherein the sample droplets comprise a dried blood spot reconstituted in a saline solution.

50. The method of claim 46 wherein the sample droplets comprise a dried blood spot reconstituted in a buffer.

51. The method of claim 46 wherein the sample droplets comprise a dried blood spot reconstituted in a solution comprising a surfactant.

52. The method of claim 51 wherein the surfactant has an HLB in the range of about 10 to about 20.

53. The method of claim 51 wherein the surfactant has an HLB in the range of about 15 to about 20.

54. The method of claim 46 wherein the sample droplets are from the same subject.

55. The method of claim 46 wherein the sample droplets are from different subjects.

56. The method of claim 46 wherein the wherein two or more of the two or more sample droplets are each combined with one or more reagent droplets selected for establishing reaction conditions for an enzyme associated with an enzyme deficiency selected from the group consisting of Pompe, Niemann-Pick, Fabry, Krabbe, and Gaucher.

57. The method of claim 1 wherein the enzyme is selected to provide diagnostic information about an enzyme deficiency.

58. The method of claim 57 wherein the enzyme deficiency is selected from lysdsomal storage diseases.

59. The method of claim 57 wherein the enzyme deficiency is selected from the group consisting of Pompe, Niemann-Pick, Fabry, Krabbe, and Gaucher.

60. The method of claim 57 further comprising providing therapeutic treatment to a subject based on the diagnostic information.

61. The method of claim 1 wherein the sample droplet comprises cultured cells and/or supernatant from a cell culture.

62. The method of claim 1 wherein the substrate comprises 4-methylumbelliferyl-α-L-iduronide, 4-methylumbelliferyl-β-D-galactoside, 4-methylumbelliferyl-β-D-glueuronic acid, 4-methylumbelliferyl-α-L-fucoside, 4-methylumbelliferyl-α-mannoside, 4-methylumbelliferyl-β-D-mannoside, 4-nitrocathecol sulfate, 4-methylumbelliferyl-β-D-N-acetylglucosaminide, 4-methylumbelliferyl-β-D-N-acetylglucosaminide sulfate, 4-methylumbelliferyl-β-D-glucosaminide, 4-methylumbelliferyl-α-D-galactoside, 4-methylumbelliferyl-α-D-neuraminic acid, 4-methylumbelliferyl-α-D-N-acetylgalactosaminide, phenolphthalein β-D-glucuronic acid, and mixtures and derivatives thereof.

63. The method of claim 1 wherein the substrate comprises a fluorophoric moiety.

64. The method of claim 63 wherein the fluorophoric moiety comprises 4-methyllumbelliferyl.

65. The method of claim 1 wherein the substrate comprises a chromophoric moiety.

66. The method of claim 65 wherein the chromophoric moiety comprises 4-nitrocathecol or phenolphthalein.

67. The method of claim 1 wherein the substrate comprises a radioactive moiety.

68. The method of claim 67 wherein the radioactive moiety comprises $^{14}C$ sphingomyelin or $^{3}H$ galactosylceramide.

69. The method of claim 1 further comprising incubating the reaction droplet for a period of less than about 12 hours.

70. The method of claim 1 further comprising controlling the temperature of the reaction droplet.

71. The method of claim 1 wherein:
(a) the sample droplet is prepared by reconstituting a dried blood spot disc having a diameter of less than about 10 mm in less than about 1000 μL of solution; and
(b) the sample is dispensed into at least 2 sample droplets.

72. The method of claim 71 further comprising reconstituting the dried blood spot disc in less than about 750 μL of solution.

73. The method of claim 71 further comprising reconstituting the dried blood spot disc in less than about 500 μL of solution.

74. The method of claim 71 further comprising reconstituting the dried blood spot disc in less than about 250 μL of solution.

75. The method of claim 71 further comprising reconstituting the dried blood spot disc in solution having a volume ranging from about 25 μL to about 750 μL.

76. The method of claim 71 further comprising reconstituting the dried blood spot disc in solution having a volume ranging from about 25 μL to about 500 μL.

77. The method of claim 71 further comprising reconstituting the dried blood spot disc in solution having a volume ranging from about 25 μL to about 250 μL.

78. The method of claim 71 further comprising reconstituting the dried blood spot disc in solution having a volume ranging from about 25 μL to about 150 μL.

79. The method of claim 71 wherein the sample is dispensed into at least 5 sample droplets.

80. The method of claim 71 wherein the sample is dispensed into at least 10 sample droplets.

81. The method of claim 71 wherein the sample is dispensed into at least 25 sample droplets.

82. The method of claim 71 wherein the dried blood spot disc has a diameter ranging from about 1 mm to about 10 mm.

83. The method of claim 71 wherein the dried blood spot disc has a diameter ranging from about 1 mm to about 8 mm.

84. The method of claim 71 wherein the dried blood spot disc has a diameter ranging from about 1 mm to about 6 mm.

85. The method of claim 71 wherein the dried blood spot disc has a diameter ranging from about 1 mm to about 4 mm.

86. The method of claim 71 wherein each sample droplet is used to conduct the method using a different enzyme.

87. The method of claim 1 wherein the sample droplet is prepared by reconstituting a dried blood spot disc having a diameter of less than about 4 mm in less than about 1000 μL of solution.

88. The method of claim 71 wherein the sample is dispensed into at least 10 sample droplets.

89. The method of claim 79 wherein each sample droplet is used to conduct the method using a different enzyme.

90. The method of claim 71 wherein:
(a) the disc has a diameter of less than about 4 mm;
(b) the disk is reconstituted in less than about 1000 μL of solution;
(c) the sample is dispensed into at least 5 sub-droplets; and
(d) at least 5 sub-droplets are each used to conduct the method using a different enzyme.

91. The method of claim 71 wherein:
(a) the disc has a diameter of less than about 8 mm;
(b) the disc is reconstituted in less than about 500 μL of solution;
(c) the sample is dispensed into at least 5 sub-droplets; and
(d) at least 5 sub-droplets are each used to conduct the method using a different enzyme.

92. The method of claim 71 wherein:
(a) the disc has a diameter of less than about 8 mm;
(b) the disc is reconstituted in less than about 200 μL of solution;
(c) the sample is dispensed into at least 5 sub-droplets; and
(d) at least 5 sub-droplets are each used to conduct the method using a different enzyme.

93. The method of claim 71 wherein:
(a) the disc has a diameter of less than about 4 mm;
(b) the disk is reconstituted in less than about 1000 μL of solution;
(c) the sample is dispensed into at least 10 sub-droplets; and
(d) at least 10 sub-droplets are each used to conduct the method using a different enzyme.

94. The method of claim 71 wherein:
(a) the disc has a diameter of less than about 8 mm;
(b) the disc is reconstituted in less than about 500 μL of solution;
(c) the sample is dispensed into at least 10 sub-droplets; and
(d) at least 10 sub-droplets are each used to conduct the method using a different enzyme.

95. The method of claim 71 wherein:
(a) the disc has a diameter of less than about 8 mm;
(b) the disc is reconstituted in less than about 200 μL of solution;
(c) the sample is dispensed into at least 10 sub-droplets; and
(d) at least 10 sub-droplets are each used to conduct the method using a different enzyme.

96. The method of claim 71 wherein:
(a) the disc has a diameter ranging from about 1 mm to about 8mm;
(b) the disc is reconstituted in solution ranging from about 25 μL to about 200 μL;
(c) the sample is dispensed into at least 5 sub-droplets; and
(d) at least 5 sub-droplets are each used to conduct the method using a different enzyme.

97. The method of claim 96 wherein the disc is prepared from a dried blood spot made using less than about 10 mL of blood.

98. The method of claim 96 wherein the disc is prepared from a dried blood spot made using less than about 1 mL of blood.

99. The method of claim 97 wherein the blood is from a newborn human infant.

100. The method of claim 97 wherein the blood is from a premature human infant.

101. The method of claim 97 wherein the blood is from a laboratory animal.

102. The method of claim 1 wherein the volume of the sample droplet ranges from about 1 nL to about 1000 nL.

103. The method of claim 1 wherein the volume of the sample droplet ranges from about 1 nL to about 1000 nL.

104. The method of claim 1 wherein the volume of the sample droplet ranges from about 1 nL to about 500 nL.

105. The method of claim 1 wherein the volume of the sample droplet ranges from about 1 nL to about 250 nL.

106. The method of claim 1 wherein the volume of each of the one or more reagent droplets ranges from about 1 nL to about 1000 μL.

107. The method of claim 1 wherein the volume of each of the one or more reagent droplets ranges from about 1 nL to about 1000 nL.

108. The method of claim 1 wherein the volume of each of the one or more reagent droplets ranges from about 1 nL to about 500 nL.

109. The method of claim 1 wherein the volume of each of the one or more reagent droplets ranges from about 1 nL to about 250 nL.

110. The method of claim 1 wherein the volume of the reaction droplet ranges from about 1 nL to about 1000 μL.

111. The method of claim 1 wherein the volume of the reaction droplet ranges from about 1 nL to about 2000 nL.

112. The method of claim 1 wherein the volume of the reaction droplet ranges from about 1 nL to about 1000 nL.

113. The method of claim 1 wherein the volume of the reaction droplet ranges from about 1 nL to about 500 nL.

114. The method of claim 1 further comprising combining the reaction droplet with a quench droplet comprising one or more quenching reagents selected to substantially stop the enzyme reaction.

115. The method of claim 114 wherein multiple reaction droplets are used to effect multiple enzyme reaction types, and a common quench droplet formulation is used to substantially stop each of the enzyme reaction types.

* * * * *